(12) United States Patent
Li et al.

(10) Patent No.: US 7,052,843 B2
(45) Date of Patent: May 30, 2006

(54) TRANSCRIPTION-BASED ASSAY FOR IDENTIFICATION OF POST-TRANSLATIONAL MODIFICATION AND ITS APPLICATION IN PROTEOMICS

(75) Inventors: Dangsheng Li, Forest Hills, NY (US); James Yopp, Jr., New York, NY (US); Herbert H. Samuels, New Rochelle, NY (US)

(73) Assignee: New York University, New York, NY (US)

( * ) Notice: Subject to any disclaimer, the term of this patent is extended or adjusted under 35 U.S.C. 154(b) by 458 days.

(21) Appl. No.: 10/267,141

(22) Filed: Oct. 8, 2002

(65) Prior Publication Data

US 2004/0067497 A1 Apr. 8, 2004

(51) Int. Cl.
| | |
|---|---|
| G01N 33/53 | (2006.01) |
| C12Q 1/68 | (2006.01) |
| C12Q 1/66 | (2006.01) |
| C12N 15/63 | (2006.01) |
| C12N 5/06 | (2006.01) |
| C07H 21/04 | (2006.01) |
| C12P 19/34 | (2006.01) |

(52) U.S. Cl. .......................... 435/6; 435/7.1; 435/7.6; 435/8; 435/320.1; 435/361; 435/325; 536/23.4; 536/23.1; 536/23.2

(58) Field of Classification Search .................... None
See application file for complete search history.

(56) References Cited

U.S. PATENT DOCUMENTS

| 5,985,664 A | 11/1999 | Baker et al. |
| 6,087,122 A | 7/2000 | Hustad et al. |
| 6,368,809 B1 | 4/2002 | Bernards |
| 2002/0019002 A1 | 2/2002 | Griffiths |
| 2002/0042083 A1 | 4/2002 | Issakani et al. |

OTHER PUBLICATIONS

Hanlon et al., "C/EBP Beta and Elk-1 Synergistically Transactivate the C-Fos Serum Response Element," *BMC Cell Biology* 1:2 (2000).

Müller, "SUMO, Ubiquitin's Mysterious Cousin," *Nature Reviews/Mol. Cell. Biol.* 2:202-210 (2001).

Müller et al., "C-Jun and p-53 Activity is Modulated by SUMO-1 Modification," *J. Biol. Chem.* 275:13321-13329 (2000).

Neill et al., "An Adenovirus E4 Gene Product Trans-activities *E2* Transcription and Stimulates Stable E2F Binding Through a Direct Association with E2F," *Proc. Natl. Acad. Sci. USA* 87:2008-2012 (1990).

Sealy et al., "Regulation of the *cfos* Serum Response Element by C/EBPβ," *Mol Cell. Biol.* 17:1744-1755 (1997).

*Primary Examiner*—David Guzo
*Assistant Examiner*—Michele Joike
(74) *Attorney, Agent, or Firm*—Nixon Peabody LLP

(57) ABSTRACT

The present invention relates to a method for detecting the post-translational modification of a target protein by a post translational modifier polypeptide molecule; a method for screening a candidate protein for E3 ligase activity; a method of screening a test compound for the ability to regulate the post-translational modification of a target protein by a post-translational modifier polypeptide molecule; and a method for the large-scale detection of candidate target proteins of post-translational modification by a modifier polypeptide molecule. The present invention also relates to a kit for determining whether a test protein is post-translationally modified by a modifier polypeptide molecule; a kit for screening a test compound for the ability to regulate the post-translational modification of a target protein by a post-translational modifier peptide molecule, and another kit for determining whether a test protein is post-translationally modified by a modifier polypeptide molecule.

44 Claims, 22 Drawing Sheets

TRANSCRIPTION-BASED ASSAY FOR IDENTIFICATION OF POST-TRANSLATIONAL MODIFICATION AND ITS APPLICATION IN PROTEOMICS

The subject matter of this application was made with support from the United States Government under National Institutes of Health Grant Nos. DK09581 and DK16636-27. The United States Government may have some rights.

FIELD OF THE INVENTION

The present invention relates to a method for detecting the post-translational modification of a target protein by a post translational modifier polypeptide molecule; a method for screening a candidate protein for E3 ligase activity; a method of screening a test compound for the ability to regulate the post-translational modification of a target protein by a post-translational modifier polypeptide molecule; a method for the large-scale detection of candidate target proteins of post-translational modification by a modifier polypeptide molecule, and kits for carrying out such methods.

BACKGROUND OF THE INVENTION

Post-translational modification of proteins is an important mechanism required for many cellular functions, including the mediation of protein-protein interactions, enzymatic activity, degradation, localization of proteins to cellular compartments, and maintenance of stability. The modifications usually occur via specific enzymatic reactions that catalyze the transfer of various chemical/molecular groups to specific amino-acid residues of target proteins. Some well known examples of post-translational modification include phosphorylation, acetylation, methylation, glycosylation, and ubiquitination. The unique feature of ubiquitination is that the moiety that is transferred to the target protein is itself a polypeptide (ubiquitin). Ubiquitination usually serves as a signal in the cell to target-modified proteins for degradation by the 26S proteosome. The molecular mechanism of ubiquitin conjugation and its regulation have been the subject of extensive studies.

A number of proteins have been discovered that share sequence similarities with ubiquitin. An early example of these proteins is "SUMO" ("small ubiquitin-like modifier"). Since its discovery several years ago, the study of SUMO-modification has evolved into a very important and productive field. Efforts have been dedicated to characterizing the enzymology of the SUMO-modification pathway and identifying target proteins for SUMO. These studies have revealed the following important features of the SUMO protein family. SUMO and the SUMO-modification pathway are highly conserved across the eukaryotes (Müller at al., "SUMO, Ubiquitin's Mysterious Cousin," *Nature Reviews/Molecular Cell Biology* 2:202–210 (2001)). While invertebrates have a single SUMO gene, the SUMO family in vertebrates consists of three genes: SUMO-1, -2, and -3. SUMO-1 (also known as Sentrin, UBL1, PIC1, and GMP1), is the prototype member of the ubiquitin-like family of protein modifiers and was isolated by several labs independently (Boddy et al., "PIC 1, A Novel Ubiquitin-Like Protein Which Interacts with the PML Component of a Multiprotein Complex that is Disrupted in Acute Promyelocytic Leukaemia," *Oncogene* 13(5):971–982 (1996); Mahajan et al., "A Small Ubiquitin-Related Polypeptide Involved in Targeting RanGAP1 to Nuclear Pore Complex Protein RanBP2," *Cell* 88:97–107 (1997); Matunis et al., "A Novel Ubiquitin-like Modification Modulates the Partitioning of the Ran-GTPase-activating Protein RanGAP1 Between the Cytosol and the Nuclear Pore Complex," *J. Cell Biol.* 135:1457–1470 (1996); Matunis et al., "SUMO-1 Modification and its Role in Targeting the RanGTPase-activating Protein, RanGAP1, to the Nuclear Pore Complex, "*J. Cell Biol.* 140:499–509 (1998); Okura et al., "Protection Against Fas/APO-1-and Tumor Necrosis Factor-Mediated Cell Death by a Novel Protein, Sentrin," *J. Immunol.* 157(10): 4277–4281 (1996); Shen et al., "UBL1, A Human Ubiquitin-Like Protein Associating with Human RAD51/RAD52 Proteins," *Genomics* 36(2):271–279 (1996)). Conjugation by SUMO-1 has received most of the research efforts, while relatively little is known about the modifications by SUMO-2 and SUMO-3. The enzymes for SUMO-modification are distinct from those involved in ubiquitination, but the overall enzymology of the SUMO-modification pathway appears to parallel that of the ubiquitin-conjugating pathway and involves a SUMO-activating enzyme ("E1"), a SUMO-conjugating enzyme ("E2"), and a ligase activity ("E3"). Examples of E3 activity have only been discovered very recently (Johnson and Gupta, "An E3-like Factor that Promotes SUMO Conjugation to the Yeast Septins," *Cell* 106: 735–744 (2001); Takahashi et al., "A Novel Factor Required for the SUMO1/Smt3 Conjugation of Yeast Septins," *Gene* 275:195–315 (2001); Kahyo et al.," Involvement of PIAS1 in the SUMO Modification of Tumor Suppressor p53," *Molecular Cell* 6: 713–718 (2001)). In contrast to ubiquitination, SUMO-modification generally does not promote the degradation of the target proteins. Instead, it appears to play important roles in modulating target protein function(s). Identified targets for SUMO-modification include proteins that play important roles in various aspects of cell function, such as tumor suppressors p53 and PML, the nuclear-pore component RanGAP1, the proto-oncogene Mdm-2, and the NF-kB regulator IkB.

SUMO-1 shows only an 18% homology to ubiquitin. SUMO-attachment to a protein substrate is reversible and usually does not result in SUMO-chain formation. Also in contrast to ubiquitination, which targets proteins for degradation, sumolation seems to enhance the stability of proteins and/or modulate specific protein-protein interactions. In addition, SUMO conjugation can also result in specific trafficking and localization of target proteins.

In an effort to identify proteins involved in double strand break repair of DNA, Shen et al., showed that SUMO-1 interacts with RAD51/RAD52, a protein complex formed during DNA repair and recombination (Shen et al., "UBL1, A Human Ubiquitin-Like Protein Associating with Human RAD51/RAD52 Proteins," *Genomics* 36(2):271–279 (1996)).

Other studies isolated SUMO-1 as a factor which binds to the 'death domain' of the Fas/APO-1 and the TNFR1 receptors and therefore, plays a role in apoptosis. These studies showed that when overexpressed, SUMO-1 provided protection against both Fas/APO-1 and TNF-induced cell death (Okura et al., "Protection Against Fas/APO-1-and Tumor Necrosis Factor-Mediated Cell Death by a Novel Protein, Sentrin," *J. Immunol.* 157(10):4277–4281 (1996)). Northern blot analysis of SUMO-1 showed expression in all tissues, with the highest levels being in the heart, skeletal muscle, testis, ovary, and thymus.

SUMO-1 was also shown to be involved in nuclear protein import by conjugating to the 70 kD nuclear pore protein RanGAP1, which could then interact with RanBP2, resulting in a complex which is necessary for nuclear protein import (Mahajan et al., "A Small Ubiquitin-Related Polypeptide Involved in Targeting RanGAP1 to Nuclear Pore Complex Protein RanBP2," *Cell* 88:97107 (1997); Matunis et al., "SUMO-1 Modification and its Role in Targeting the RanGTPase-activating Protein, RanGAP1, to the Nuclear Pore Complex," *J. Cell Biol.* 140:499–509 (1998)). It has been shown that SUMO-1 conjugation is carried out by Ubc9, an enzyme equivalent to the E2 enzyme of ubiquitin conjugating pathways (Gong et al., "Preferential Interaction of Sentrin with a Ubiquitin-Conjugating Enzyme, Ubc9," *J. Biol. Chem.* 272(45):28198–28201 (1997); Johnson and Blobel, "Ubc9p is the Conjugating Enzyme for the Ubiquitin-Like Protein Smt3p," *J. Biol. Chem.* 272:26799–26802 (1997); Lee et al., "Modification of Ran GTPase-activating Protein by the Small Ubiquitin-Related Modifier SUMO-1 Requires Ubc9, an E2-type Ubiquitin-Conjugating Enzyme Homologue," *J. Biol. Chem.* 273:6503–6507 (1998); Saitoh et al., "Ubc9p and the Conjugation of SUMO-1 to RanGAP1 and RanBP2," *Curr. Biol.* 8:121–124 (1998); Schwarz et al., "The Ubiquitin-Like Proteins SMT3 and SUMO-1 are Conjugated by the UBC9 E2 Enzyme," *Proc. Natl. Acad. Sci. USA* 95(2):560–564) (1998)). SUMO-1 interaction and modification have also been documented for the tumor suppressor protein PML and its nuclear body partner Sp100 (Boddy et al., "PIC 1, A Novel Ubiquitin-Like Protein Which Interacts with the PML Component of a Multiprotein Complex that is Disrupted in Acute Promyelocytic Leukaemia," *Oncogene* 13(5):971–982 (1996); Stemsdorf et al., "Evidence for Covalent Modification of the Nuclear Dot-Associated Proteins PML and Sp100 by PIC1/SUMO-1," *J. Cell Biol.* 139(7):1621–1634 (1997)). Other examples of targets of SUMO modification include the tumor suppressor p53, the proto-oncogene Mdm2, and the NF-kappaB regulator I-kappaB (Müller at al., "SUMO, Ubiquitin's Mysterious Cousin," *Nature Reviews/Molecular Cell Biology* 2:202–210 (2001)).

Those protein modifiers which are called 'ubiquitin-like' modifiers ("UBLs"), of which SUMO is a prime example, function as modifiers in a manner analogous to ubiquitin, i.e., the modifier protein is conjugated to the protein it is modifying. Other examples of UBLs include NEDD8 and Apgl2 (Müller at al., "SUMO, Ubiquitin's Mysterious Cousin," *Nature Reviews/Molecular Cell Biology* 2:202–210 (2001)). A second group of proteins, designated 'ubiquitin-domain proteins' ("UDPs"), have been identified containing domains that are related in sequence to ubiquitin. In contrast to UBLs, UDPs do not conjugate to other proteins (Müller at al., "SUMO, Ubiquitin's Mysterious Cousin," *Nature Reviews/Molecular Cell Biology* 2:202–210 (2001)).

Given the importance of SUMO-modification (referred to here as sumolation), identification of additional SUMO targets are certainly of great research interest, which should not only reveal more aspects of cellular life regulated by SUMO-modification, but may also provide novel clues for developing therapeutic drugs that intervene or regulate these important cellular processes. Currently, there are only two main approaches for detecting SUMO-modification. The in vitro assay attempts to reconstitute the modification reaction using purified or partially purified components (either from cell extracts or from a recombinant source) such as GST-SUMO, GST-UBC9 (the E2 enzyme), and the E1 enzyme. The protein to be tested is usually in a radio-labeled form (e.g., produced from in vitro translation) or in a purified recombinant form. If the test protein undergoes sumolation, the modified form migrates more slowly than the apo-form in SDS-PAGE, which can be detected by either Western blot or autoradiography. However, this in vitro approach is generally inefficient, either due to the intrinsic property of the modification system, or, more likely, due to the lack of E3 activity in the in vitro reactions. The potential problem of lack of E3 activity may not be easily solved, despite the recent identification of the first examples of E3 activities for the SUMO-conjugation pathway. The ubiquitination pathway employs a large number of distinct E3 enzymes, which is understandable, given the fact that substrate proteins are diverse, and that E3 plays an important role in the recognition of substrate specificity. Thus, it is likely that many E3s for the SUMO-pathway remain to be discovered.

The second current approach attempts to directly detect SUMO-modification of candidate proteins in cells. Usually, the candidate protein (either expressed endogenously or by transfection) is immunoprecipitated from cell lysates by an appropriate antibody ("Ab"), resolved on an SDS-PAGE, and then Western-blotted using an appropriate Ab against this protein and/or against SUMO. The advantage of this in vivo system is that the modification reaction occurs in the cell and utilizes the cellular enzymatic system. Nevertheless, there are several potential drawbacks to this approach: 1) the feasibility to carry out this approach is limited by the availability of appropriate Abs that exhibit desired specificity and sensitivity; 2) the isopeptide bond of sumolation is very sensitive to protease attack and can be rapidly lost during cell lysis; 3) the relatively harsh conditions that are used to lyse the cells in order to inactive these proteases can further limit the utilization of appropriate Abs to carry out the analysis; and 4) currently published studies usually show that even though a candidate protein is SUMO-modified in cells, the detectable sumolated form is only a very small portion of the total candidate protein. Therefore, the sensitivity of the detection is also an issue in existing methods.

While much is known about SUMO and other factors involved in post-translational modification of cellular proteins, there are currently no dependable methods of identifying proteins which are post-translational modifiers (termed here as "post-translational modifier polypeptides", or "PMPs"), regulators of PMPs, or target proteins of PMPs. The present invention seeks to overcome these and other deficiencies in the art.

SUMMARY OF THE INVENTION

The present invention relates to an assay method for detecting the post-translational modification of a target protein ("TP") by a post translational modifier polypeptide molecule ("PMP"). This involves providing a first cell containing a first plasmid having an expression unit comprising: a first nucleic acid molecule encoding a DNA binding domain ("DBD") which is operably linked to a second nucleic acid molecule encoding a target protein, wherein expression of the DNA binding domain and target protein in the cell produces a DBD-TP fusion protein; a second plasmid having an expression unit comprising a first nucleic acid molecule encoding a reporter protein operably linked to a second nucleic acid molecule encoding a DNA binding site ("DBS") to which the DNA binding domain of the DNA binding domain-TP fusion protein is capable of binding, and wherein expression of the reporter protein is under the control of the DBS; and a third plasmid having an expression unit comprising a first nucleic acid molecule encoding a transcription activation domain ("ACT") which is operably linked to a second nucleic acid molecule encoding a known or suspected PMP, wherein expression of the ACT and PMP in cells produces a ACT-PMP fusion protein. This method also involves providing a second cell containing the first and second plasmids and a fourth plasmid. The fourth plasmid has an expression unit with a first nucleic acid molecule encoding an ACT operably linked to a second nucleic acid molecule encoding a mutant form of the PMP ("PMPmut") that is defective or deficient in effecting post-translational modification of the target protein, wherein expression of the ACT and PMPmut in the cell produces a ACT-PMPmut fusion protein. The first and second cells are cultured under conditions effective for post-translational modification of the target protein to occur. Reporter activity in the first and second cells is determined. An increase in reporter activity in the first cell compared to the second cell indicates that the target protein has undergone post-translational modification by the post-translational modifier polypeptide molecule.

The present invention also relates to a method for screening a candidate protein for E3 ligase activity. This involves providing a first cell containing: a first plasmid having an expression unit with a first nucleic acid molecule encoding a DNA binding domain operably linked to a second nucleic acid molecule encoding a target protein, where the expression of the DBD and TP in the cell produces a DBD-TP fusion protein; a second plasmid having an expression unit with a first nucleic acid molecule encoding a reporter protein operably linked to a second nucleic acid molecule encoding a DNA binding site ("DBS") to which the DNA binding domain of the DBD-TP fusion protein of the first plasmid is capable of binding, with expression of the reporter protein under the control of the DBS; a third plasmid having an expression unit with a first nucleic acid molecule encoding an ACT operably linked to a second nucleic acid molecule encoding a known or suspected PMP, and expression of the ACT and PMP in the cell produces a ACT-PMP fusion protein; and a fourth plasmid having a nucleic acid molecule encoding a candidate E3 ligase. This method also involves providing a second cell containing the first, second, and third plasmids, and a fifth plasmid. The fifth plasmid has an expression unit having no nucleic acid molecule insert. The first and second cells are cultured under conditions effective for post-translational modification of the target protein to occur. Reporter activity is determined in the first and second cells. An increase in reporter activity in the first cell compared to the second cell indicates that the candidate E3 ligase has E3 ligase activity.

The present invention also relates to a method of screening a test compound for the ability to regulate the post-translational modification of a TP by a PMP molecule. This method involves providing first and second cells containing: a first plasmid having an expression unit with a first nucleic acid molecule encoding a DBD that is operably linked to a second nucleic acid molecule encoding a TP, wherein expression of the DBD and TP in the cells produces a DBD-TP fusion protein; a second plasmid having an expression unit with a first nucleic acid molecule encoding a first reporter protein that is operably linked to a second nucleic acid molecule encoding a DBS to which the DBD of the DBD-TP fusion protein is capable of binding, and where expression of the reporter protein is under the control of the DBS; and a third plasmid having an expression unit with a first nucleic acid molecule encoding an ACT operably linked to a second nucleic acid molecule encoding a PMP capable of effecting post-translation modification of the TP, where expression of the ACT and PMP in the cells produces an ACT-PMP fusion protein. The first and second cells are cultured under conditions effective for post-translational modification of the TP to occur. The first cell is contacted with a test compound under conditions effective to allow the regulation of post-translational modification of the target protein to occur. The activity of the reporter in the first and second cells is determined. The activity of the first reporter in the first cell is normalized for non-specific effect of the test compound, and a change in reporter activity in the first cell compared to the second cell, after normalizing, indicates that the test compound regulates the post-translational modification of the TP by the PMP.

The present invention also relates to a method for the large-scale detection of candidate target proteins of post-translational modification by a modifier polypeptide molecule. This involves providing a cell system in a multiwell device, with the system having a plurality of first cells containing a first expression unit having a first nucleic acid molecule encoding a reporter protein operably linked to a second nucleic acid molecule encoding a DBS, wherein expression of the reporter protein is under the control of the DBS; and a second expression unit having a first nucleic acid molecule encoding an ACT operably linked to a second nucleic acid molecule encoding a known or suspected PMP, wherein expression of the ACT and PMP in the cells produces a ACT-PMP fusion protein. The cell system also contains a plurality of second cells containing the first expression unit and a third expression unit. The third expression unit has a first nucleic acid molecule encoding an ACT that is the same as that encoded by the second expression unit operably linked to a second nucleic acid molecule encoding a PMPmut of the first cell that is defective or deficient in effecting post-translational modification of target proteins, and expression of the ACT and PMPmut in the cells produces a ACT-PMPmut fusion protein. The first and second cells are placed into different wells of the multiwell device. Also provided is a plurality of additional expression units, each having a first nucleic acid molecule encoding a DBD operably linked to a second nucleic acid molecule encoding a candidate target protein ("CTP"), wherein the DBD is capable of binding to the DBS of the first expression unit of the cell system, and at least some of the plurality of these additional expression units contain genes encoding different CTPs. Furthermore, for at least some of the plurality of these additional expression units, expression of the DBD and CTP in the cells produces a DBD-CTP fusion protein. The first and second cells are transfected with the additional expression units. The first and second cells are cultured under conditions effective for post-translational modification to occur and reporter activity in each well in the multiwell system is measured. The reporter activity of the first cells is compared to the reporter activity of the second cells for each CTP. Post-translationally modified CTPs are identified as those that exhibit an increase in reporter activity in the first cells compared to the second cells.

The present invention also relates to an assay kit for determining whether a test protein is post-translationally modified by a modifier polypeptide molecule. This kit includes a first plasmid which has an expression unit with a first nucleic acid molecule encoding a DBD, and which allows for a second nucleic acid molecule encoding a TP to be inserted so that expression of the DBD and TP in a cell produces a DBD-TP fusion protein. This kit also includes a second plasmid having an expression unit with a first nucleic acid molecule encoding a reporter protein operably linked to a second nucleic acid molecule encoding a DBS to which the DBD encoded in the first plasmid is capable of binding, and wherein expression of the reporter protein is under the control of the DBS. Also included in the kit is a third plasmid having an expression unit with a first nucleic acid molecule encoding an ACT operably linked to a second nucleic acid molecule encoding a PMP, wherein expression of the ACT and PMP in a cell produces a ACT-PMP fusion protein. A fourth plasmid is also included in the kit. The fourth plasmid has an expression unit with a first nucleic acid molecule encoding an ACT operably linked to a second nucleic acid molecule encoding a PMPmut that is defective or deficient in effecting post-translational modification of target proteins, where expression of the ACT and PMPmut in a cell produces a ACT-PMPmut fusion protein.

The present invention also relates to a kit for screening a test compound for the ability to regulate the post-translational modification of a TP by a PMP molecule. This kit contains a first cell having a first plasmid having a first nucleic acid molecule encoding a DBD operably linked to a second nucleic acid molecule encoding a TP, wherein expression of the DBD and TP in the cell produces a DBD-TP fusion protein. The first cell also contains a second plasmid having a first nucleic acid molecule encoding a first reporter protein operably linked to a second nucleic acid molecule encoding a DNA binding site to which the DBD of the DBD-TP fusion protein of the first plasmid is capable of binding, where expression of the first reporter protein is under the control of the DBS. The first cell also contains a third plasmid having a first nucleic acid molecule encoding an ACT operably linked to a second nucleic acid molecule encoding a PMP where expression of the ACT and PMP in the cell produces a ACT-PMP fusion protein.

The present invention also relates to an assay kit for determining whether a test protein is post-translationally modified by a modifier polypeptide molecule. This kit contains a first plasmid which has a first nucleic acid molecule encoding a DBD, and which allows for a second nucleic acid molecule encoding a TP to be inserted so that expression of the DBD and TP in a cell produces a DBD-TP fusion protein. Also provided is a first cell having a second plasmid with a first nucleic acid molecule encoding a reporter protein operably linked to a second nucleic acid molecule encoding a DBS to which the DBD encoded in the first plasmid is capable of binding, and where expression of the reporter protein is under the control of the DBS. The first cell also contains a third plasmid having a first nucleic acid molecule encoding an ACT operably linked to a second nucleic acid molecule encoding a PMP, where expression of the ACT and PMP in cells produces an ACT-PMP fusion protein. The kit also includes a second cell containing the second plasmid and a fourth plasmid. The fourth plasmid contains a first nucleic acid molecule encoding an ACT operably linked to a second nucleic acid molecule encoding a mutant form of the PMP of the third plasmid that is defective or deficient in effecting post-translational modification of a TP, wherein expression of the ACT and PMPmut in the cell produces a ACT-PMPmut fusion protein.

The present invention has several advantages over current methods of detecting or identifying aspects of post-translational modification by a PMP as follows: 1) it provides an assay carried out in live cells under culture conditions, and therefore, utilizes the cellular enzymatic system; 2) it provides a simple and rapid assay that is less time-consuming than the current assays, and eliminates the requirement for specific antibodies; 3) it is potentially more sensitive than the current assays; 4) in addition to identifying potential targets of modification by a PMP, it can also be used to identify novel E3 ligases for the sumolation or other PMP modification pathways; 5) it can be scaled up to screen a large number of candidate target proteins for potential post-translational modification by a PMP in cells, and thus has important potential in functional genomics and proteomics; and 6) it provides a method to screen a large number of compounds for identification of candidate compound(s) capable of modulating cellular modification pathway(s) of a PMP.

BRIEF DESCRIPTION OF THE DRAWINGS

FIG. 1A shows the results of formation of a covalent complex (i.e. DBD-TP-PMP-ACT) due to the post-translational modification of TP in the first cell, and the corresponding expression of the reporter gene by the transactivation domain ("ACT") of the covalent complex. FIG. 1B shows the minimal reporter activity generated in the second cell having a post-translational modifier molecule which has been mutated ("PMPmut") to abolish its ability to modify TP. "DBD" designates the DNA-binding domain in each cell, "DBS" is the corresponding DNA-binding site, and "reporter" designates the reporter gene in each cell.

FIG. 2A shows that only minimal reporter activity is generated in the first cell due to the failure of the modifier molecule to modify TP and trigger the formation of the covalent complex. FIG. 2B shows that the same amount of reporter activity is generated in the second cell containing the PMPmut as is generated in the first cell.

In FIGS. 3A–B, both the first and the second cells contain a TP that is a substrate for the PMP molecule. FIG. 3A shows the result of a first cell having an additional plasmid expressing a candidate E3 ligase. FIG. 3B shows the result of a second cell having a control plasmid that does not express the E3 ligase. FIGS. 3C–D show the results of using a third and fourth cells as controls, in which the functional modifier "PMP" has been replaced with a null modifier molecule "PMPmut. " FIG. 3C shows the result when a functional E3 ligase is additionally expressed in the third cell. FIG. 3D shows the result when no additional E3 ligase is expressed.

FIG. 4A shows that test compound "X" has an enhancing effect on the post-translational modification of the TP by the modifier molecule in the first cell, resulting in an increase in reporter activity compared to FIG. 4B, which shows the control cell which has the same components, but without the contact with compound "X."

FIG. 5A shows that test compound "Y" effects a reduction in the post-translational modification of the target protein by the modifier molecule in the first cell, as seen by a decrease in reporter activity in FIG. 5A compared with FIG. 5B, which shows the expected result in the control cell which has the same components, but without the contact with compound "Y."

FIG. 6A shows the reporter 2 activity generated when the first test cell is treated with test compound "X" or "Y. " FIG. 6B shows the reporter 2 activity generated in the second, control cell, which has the same plasmids as the first cell, but is not treated with test compound "X" or "Y." Any change in the reporter 2 activity in the first cell over the second cell is a non-specific effect generated by the test compound.

" FIG. 7A shows the reporter activity generated by candidate target proteins X, Y, and Z, which are tested in a first cell expressing a functional PMP molecule. FIG. 7B shows the result of examining candidate target proteins X, Y, and Z in a second cell which contains a null modifier molecule. Only candidate target "Y" generates more reporter activity in the first cell compared with the second cell, indicating that Y is a substrate for the PMP.

DETAILED DESCRIPTION OF THE INVENTION

The present invention relates to an assay method for detecting the post-translational modification of a target protein ("TP") by a post translational modifier polypeptide molecule ("PMP"). This involves providing a first cell containing a first plasmid having an expression unit comprising: a first nucleic acid molecule encoding a DNA binding domain ("DBD") which is operably linked to a second nucleic acid molecule encoding a target protein, wherein expression of the DNA binding domain and target protein in the cell produces a DBD-TP fusion protein; a second plasmid having an expression unit comprising a first nucleic acid molecule encoding a reporter protein operably linked to a second nucleic acid molecule encoding a DNA binding site ("DBS") to which the DNA binding domain of the DNA binding domain-TP fusion protein is capable of binding, and wherein expression of the reporter protein is under the control of the DBS; and a third plasmid having an expression unit comprising a first nucleic acid molecule encoding a transcription activation domain ("ACT") which is operably linked to a second nucleic acid molecule encoding a known or suspected PMP, wherein expression of the ACT and PMP in cells produces a ACT-PMP fusion protein. This method also involves providing a second cell containing the first and second plasmids and a fourth plasmid. The fourth plasmid has an expression unit with a first nucleic acid molecule encoding an ACT operably linked to a second nucleic acid molecule encoding a mutant form of the PMP ("PMPmut") that is defective or deficient in effecting post-translational modification of the target protein, wherein expression of the ACT and PMPmut in the cell produces a ACT-PMPmut fusion protein. The first and second cells are cultured under conditions effective for post-translational modification of the target protein to occur. Reporter activity in the first and second cells is determined. An increase in reporter activity in the first cell compared to the second cell indicates that the target protein has undergone post-translational modification by the post-translational modifier polypeptide molecule.

This embodiment of the present invention is shown in FIGS. 1A–B and FIGS. 2A–B.

Figure 1A:
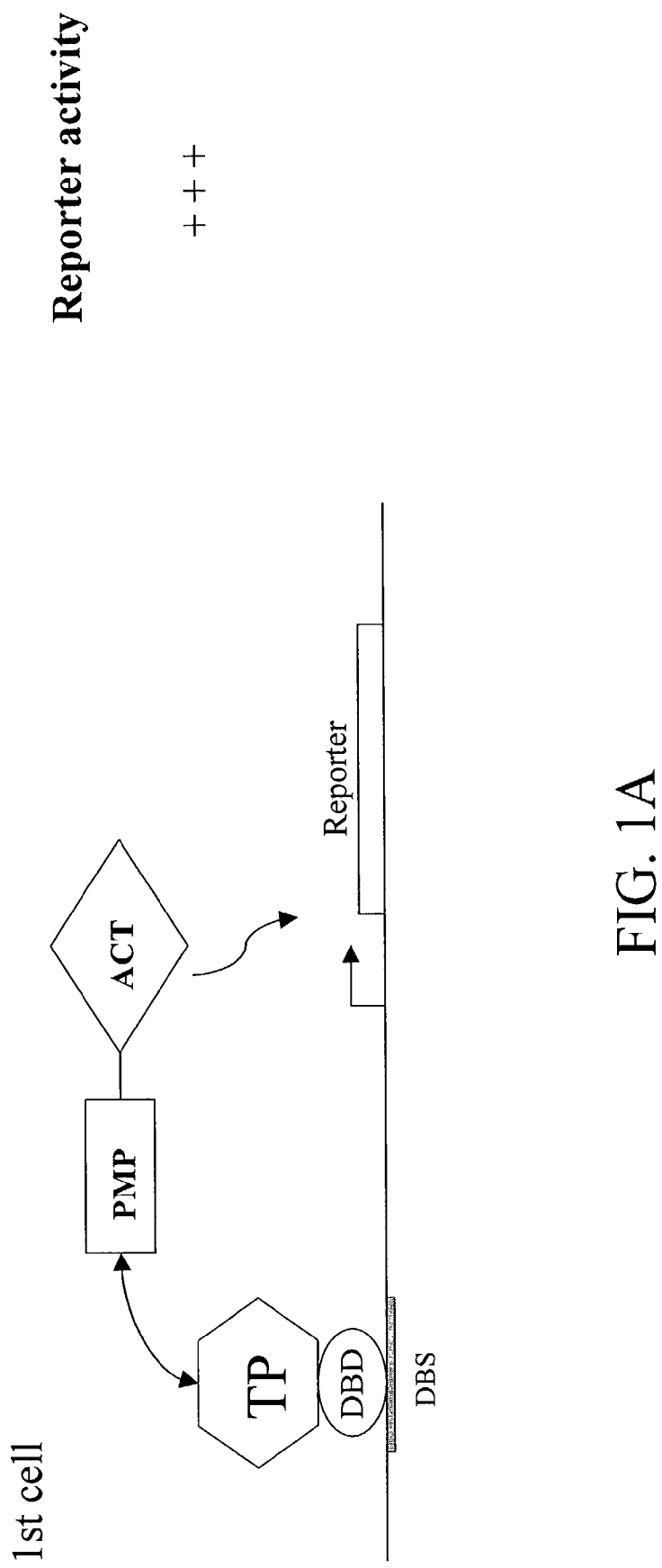
FIGS. 1A–B are schematic drawings showing the use of a target protein ("TP") that is a suitable substrate of post-translational modification by the post-translational modifier polypeptide molecule ("PMP").

Here, co-transfection of the first cell with the first, second, and third plasmids results in a measurable increase in activation of the reporter gene, as shown in FIG. 1A, if the TP expressed from the first plasmid is a target molecule for post-translational modification by the PMP molecule expressed from the third plasmid. When the first cell is transfected with the first, second, and third plasmids, the DBD-TP fusion protein is expressed from the first plasmid, while expression of the reporter protein from the second plasmid is regulated by the DBS. The presence of the third plasmid leads to expression of an ACT-PMP fusion protein. The ACT-PMP fusion protein triggers the post-translational modification of the target protein, in which the PMP moiety covalently interacts with the TP moiety of the DBD-TP fusion protein, while the DBD moiety will "find," and bind to, its cognate DBS present in the second plasmid. As shown in FIG. 1A, the binding of the DBD to the DBS brings a covalent complex ("DBD-TP-PMP-ACT") to the proximity of the promoter of the reporter gene, rendering expression of the reporter under the control of the ACT, which results in a measurable up-regulation of the reporter gene. This transcription-based assay is potentially very sensitive. Even if only a small portion of the DBD-TP fusion is modified in cells, the signal may be amplified subsequently by the use of a potent transactivation domain, such as VP16, through multiple rounds of transcription, resulting in a detectable activation of reporter activity. Although a DBD-TP should ideally be transcriptionally inert, it is expected that a modest activation or repression of reporter by a DBD-TP should not interfere with the present invention. To ensure this, controls are provided in the present invention.

Figure 1B:
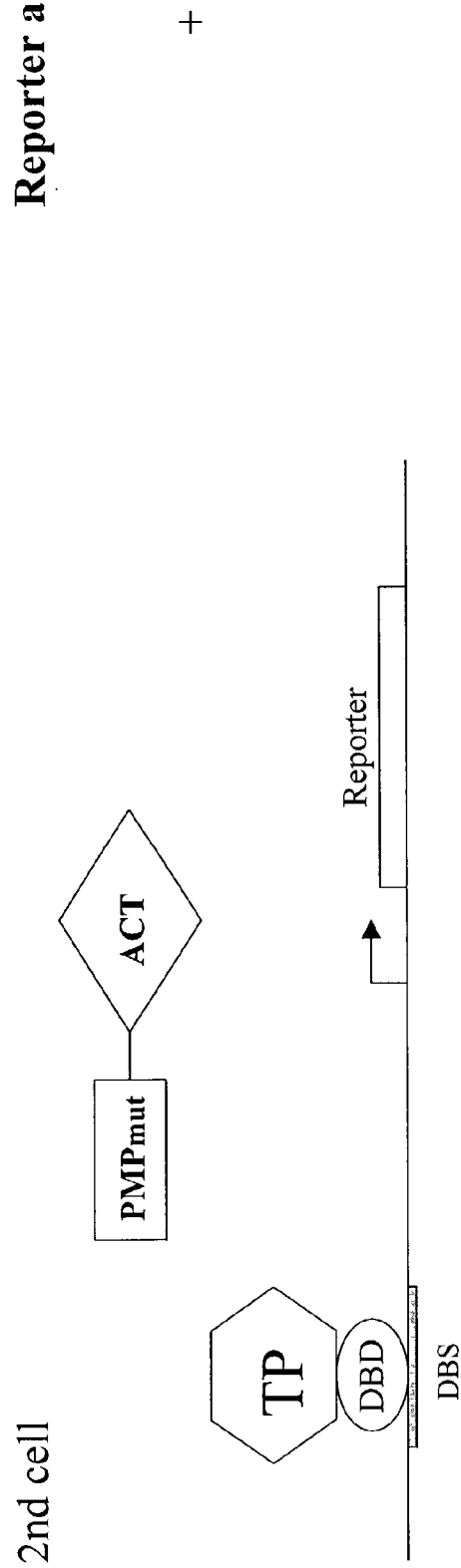
Figure 2A:
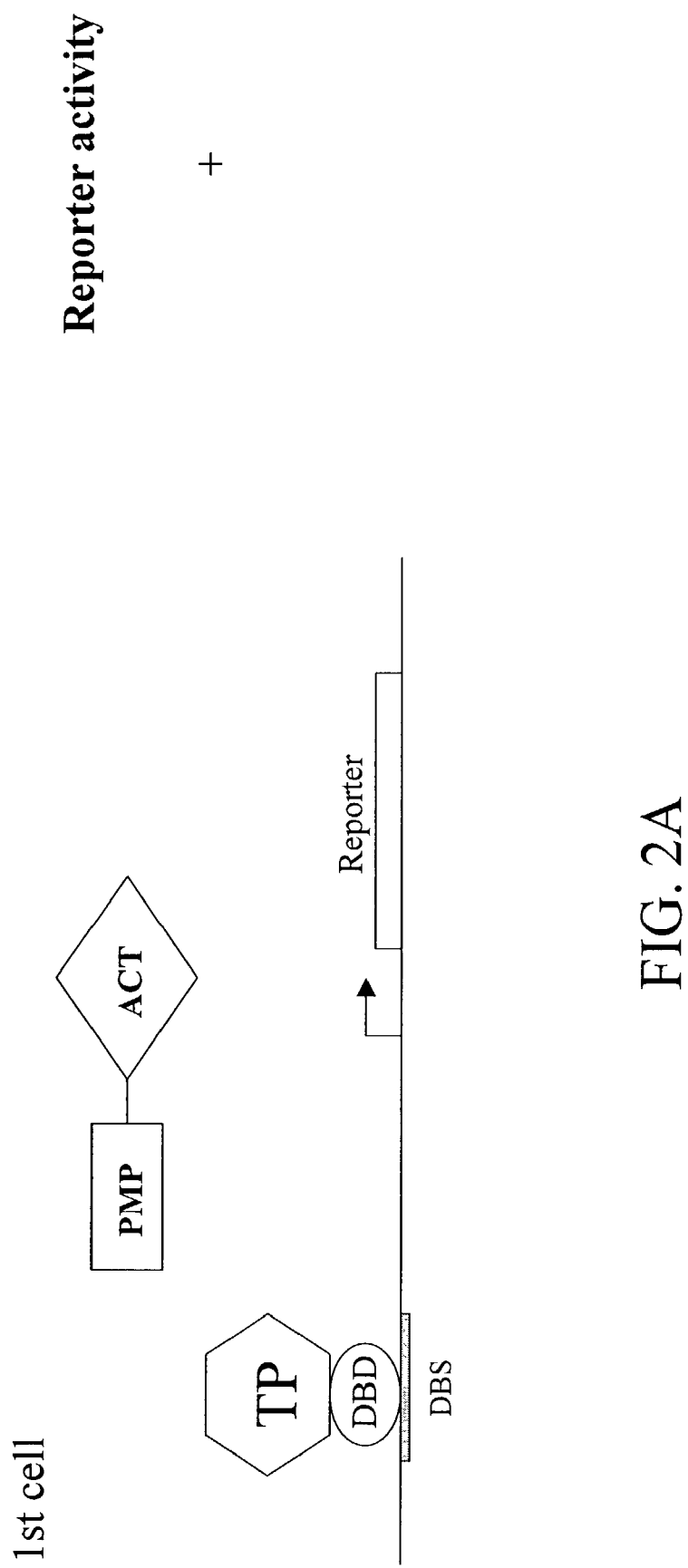
FIGS. 2A–B are schematic drawings showing the use of a target protein that is not a substrate for the modifier molecule.
Figure 2B:
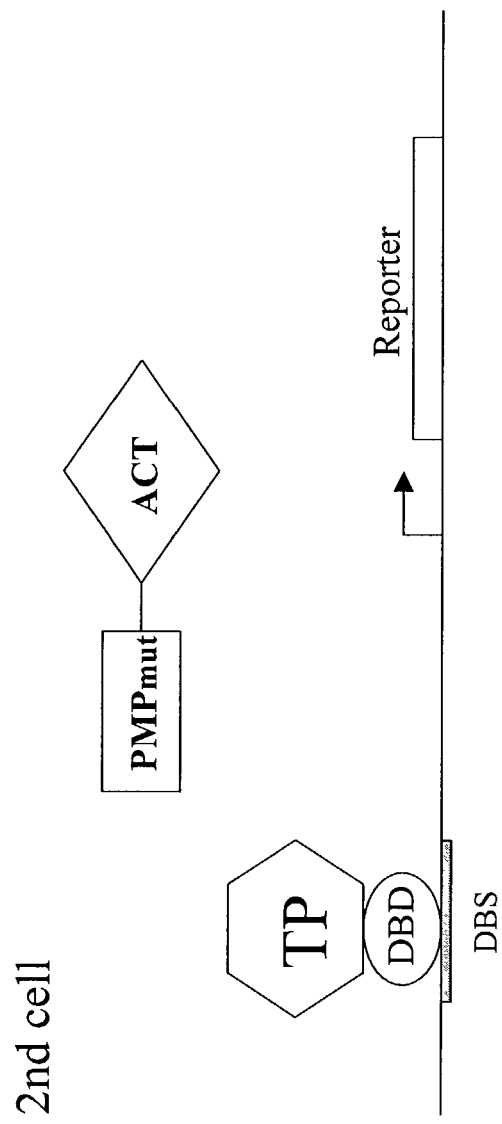

The co-transfection of the second cell with the first, second, and fourth plasmids of this aspect of the present invention serves as a control in the detection assay. A mutant, or null, version of the PMP molecule (PMPmut) encoded in the fourth plasmid, lacking the ability to covalently attach to the TP expressed from the first plasmid, will result in the scheme shown in FIG. 1B. As seen in FIG. 1B, the PMPmut is unable to covalently attach to the target protein. Therefore, while the DBD-TP binds to the DBS, no activation of the reporter occurs, because the reporter gene remains under the control of only the minimal promoter. As shown in FIGS. 2A–B, there will be no increase in the expression of the reporter gene in the first cell, shown in FIG. 2A, compared to the second cell, shown in FIG. 2B, if the examined target protein is not a suitable substrate for modification by the post-translational modifier molecule encoded in the third plasmid. The reporter activity in both cells is expected to be minimal, because the post-translational modifier polypeptide molecule is unable to covalently attach to the TP, and the reporter remains under the control of only the minimal promoter element.

The first plasmid of this aspect of the present invention contains a nucleic acid molecule encoding a TP which is a potential candidate for post-translational modification by a post-translational modifier polypeptide molecule. A target protein of the present invention is any protein of interest which is potentially capable of being post-translationally modified by a protein which is known or suspected to post-translationally modify cellular proteins. Exemplary target proteins of the present invention include, without limitation, p53, PML, RanGAP1, Mdm2, and IκB. The first plasmid also contains another nucleic acid molecule encoding a DBD. The nucleic acid molecule encoding the TP is inserted in the first plasmid in such a way that expression of the DBD and TP in cells produces a DBD-TP fusion protein. The present invention makes use of the modular nature of transcriptional activators, which are usually composed of a DNA binding domain and a separable activation domain. Activation of transcription by transcription factors requires a DNA binding region (domain) and an activation domain that activates gene transcription. These two domains can function even when present in two different molecules if the two molecules interact. In this aspect of the present invention, a suitable DNA binding domain of the present invention is any separable DNA binding domain of any transcriptional activator or repressor, including, without limitation, a DBD from a Gal4 (yeast derived) transcriptional activator and a DBD from a LexA (bacteria derived) transcriptional repressor. When the LexA DBD is chosen, a suitable option is to express in the first plasmid a LexA DBD fused in-frame to a functional nuclear localization signal ("NLS"). In this configuration, the LexA fusion protein ultimately formed is capable of translocation into the nucleus.

In this aspect of the present invention, the first cell also contains a second plasmid which has a first nucleic acid molecule encoding a reporter protein operably linked to a second nucleic acid molecule encoding a DBS to which the DBD encoded in the first plasmid is capable of binding, wherein expression of the reporter protein is under the control of the DBS. Reporter proteins suitable for this aspect of the present invention include, without limitation, chloramphenicol acetyltransferase ("CAT"), luciferase, LacZ, green fluorescent protein ("GFP"), and β-glucuronidase ("GUS").

The first cell in this aspect of the present invention also contains with a third plasmid containing a first nucleic acid molecule encoding an ACT operably linked to a second nucleic acid molecule encoding a known or suspected PMP, wherein expression of the ACT and PMP in cells produces a ACT-PMP fusion protein. Examples, without limitation, of nucleic acid molecules encoding a PMP of the present invention are nucleic acid molecules that encode the NEDD8 protein, the Apg12 protein, or a derivative thereof; any proteins or polypeptides of the SUMO family, including SUMO-1, SUMO-2, SUMO-3, SUMO-G96, SUMO-G97, and derivatives thereof; or any proteins or polypeptides of the ubiquitin family, or a derivative thereof.

SUMO G97 is a truncated form of SUMO that can modify target proteins without the pre-requirement of cleavage by the C-terminal hydrolase, while SUMO G96 is a further truncation that can no longer modify target proteins. Since SUMO G97 bypasses the requirement for the C-terminal hydrolase, substitution of wild type SUMO ("SUMO WT") with SUMO G97 in the present invention may further increase the sensitivity of the assay.

Transcription activation domains suitable for use in the third plasmid of this aspect of the present invention include, without limitation, the Gal4 activation domain derived from yeast (Ma and Ptashne, "A New Class of Yeast Transcriptional Activators," *Cell* 51: 113–119 (1987); Cheng-Ting et al., "The Two-Hybrid System: A Method to Identify and Clone Genes for Proteins that Interact with a Protein of Interest," PNAS 88: 9578–9582 (1991), which are hereby incorporated by reference in their entirety); viral protein 16 ("VP-16"), a potent Herpes derived transactivation domain (Sadowski et al., "GAL4-VP16 Is An Unusually Potent Transcriptional Activator," *Nature* 335:563–564 (1988), which is hereby incorporated by reference in its entirety); and B42, an 88-residue *E. coli* transactivator (Gyuris et al., "Cdi1, A Human G1 and S Phase Protein Phosphatase That Associates With Cdk2," *Cell* 75:791–903 (1993); Golemis et al., "Two Hybrid Systems/Interaction Traps", In F. M. Ausubel et al., *Current Protocols in Molecular Biology* p.13.14.1–13.14.17, John Wiley & Sons, New York (1994), which are hereby incorporated by reference in their entirety), which is a weaker transcriptional activator (relative to the GAL4 AD).

In this aspect of the present invention a second cell is also provided, which is transfected with the first and second plasmids described above. The second cell is additionally transfected with a fourth plasmid containing a first nucleic acid molecule encoding a transcription activation domain and a second nucleic acid molecule encoding a PMPmut that is defective or deficient in effecting post-translational modification of the target protein, where expression of the ACT and PMPmut in cells produces a ACT-PMPmut fusion protein. The PMP polypeptide molecule of the fourth plasmid can be mutated by any means known to those in the art, for example, using one of several methods of site-directed mutagenesis as described by Cosby et al., "Site-Directed Mutagenesis," *Promega Notes Magazine* 61:12 (1997); Jones and Winistorfer, "Recombinant Circle PCR and Recombination PCR for Site-Specific Mutagenesis Without PCR Product Purification," *Biotechniques* 12:528–534 (1992), which are hereby incorporated by reference in their entirety. When the PMP is a SUMO family protein, an example of a suitable mutant polypeptide is SUMO-GA. SUMO GA is identical to the wild-type SUMO polypeptide ("SUMO WT"), except for a single point mutation (Gly 97 to Ala) that abolishes the ability of the polypeptide to covalently modify target proteins. The first and second cells are then cultured under conditions effective for post-translational modification of the target protein to occur, and the activity of the reporter protein in both cells is determined. An increase in reporter activity in the first cell compared to the second cell indicates that the target protein has undergone post-translational modification by the PMP polypeptide molecule expressed from the third plasmid. Determination of reporter activity is carried as suitable for the particular reporter gene selected for inclusion in the second plasmid. Such methods are well known in the art.

Once a suitable test protein, DNA binding domain and corresponding DNA binding site, post-translational modifier polypeptide molecules (wild-type and mutant), reporter protein, and transactivation domain are selected for the first aspect of the present invention, the plasmids of the present invention are prepared by incorporating the nucleic acid molecules encoding the molecules choice into a suitable vector and subsequent propagation of the plasmids in suitable host cells. This involves the practice of conventional recombinant DNA technology. Generally, this involves first inserting the nucleic acid molecule into an expression system to which the nucleic acid molecule is heterologous (i.e., not normally present). When suitable, the heterologous nucleic acid molecule is inserted into the expression system which includes the necessary elements for the transcription and translation of the inserted protein coding sequences, producing what is termed herein an "expression unit."

The nucleic acid molecules of the present invention may be inserted into any of the many available expression vectors using reagents that are well known in the art. Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), and any derivatives thereof. In preparing the expression units of the present invention, the various nucleic acid molecules of the present invention may be inserted or substituted into a bacterial plasmid-vector. Any convenient plasmid may be employed, which will be characterized by having a bacterial replication system, a marker which allows for selection in a bacterium and generally one or more unique, conveniently located restriction sites. Numerous plasmids, referred to as transformation vectors, are available for transformation. The selection of a vector will depend on the preferred transformation technique and target cells for transfection. The selected and prepared nucleic acid molecules of the present invention are cloned into the vector using standard cloning procedures in the art, such as those described by Sambrook et al., *Molecular Cloning: A Laboratory Manual*, Second Edition, Cold Spring Harbor Press, N.Y. (1989), and Ausubel, F. M. et al. (1989) *Current Protocols in Molecular Biology*, John Wiley & Sons, New York, N.Y., which are hereby incorporated by reference in their entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the plasmid-vector constructs of the present invention. These include non-transcribed regions of the vector and 5' and 3' untranslated regions, which interact with host cellular proteins to carry out transcription and translation. Such elements may vary in their strength and specificity. Depending on the vector system and host utilized, any number of suitable transcription and/or translation elements, including constitutive, inducible, and repressible promoters, as well as minimal 5' promoter elements may be used.

A constitutive promoter is a promoter that directs constant expression of a gene in a cell. Examples of some constitutive promoters that are widely used for inducing expression of transgenes include the nopoline synthase ("NOS") gene promoter, from *Agrobacterium tumefaciens* (U.S. Pat. No. 5,034,322 issued to Rogers et al., which is hereby incorporated by reference in its entirety), the cauliflower mosaic virus ("CaMV") 35S and 19S promoters (U.S. Pat. No. 5,352,605 issued to Fraley et al., which is hereby incorporated by reference in its entirety), those derived from any of the several actin genes, which are known to be expressed in most cells types (U.S. Pat. No. 6,002,068 issued to Privalle et al., which is hereby incorporated by reference in its entirety), and the ubiquitin promoter ("ubi"), which is the promoter of a gene product known to accumulate in many cell types. Examples of constitutive promoters for use in mammalian cells include the RSV promoter derived from Rous sarcoma virus, the CMV promoter derived from cytomegalovirus, and the EF1α promoter derived from the cellular elongation factor 1α gene.

Also suitable as a promoter in the third and fourth plasmids in this aspect of the present invention is a promoter that allows for external control over the regulation of gene expression. One way to regulate the amount and the timing of gene expression is to use an inducible promoter. Unlike a constitutive promoter, an inducible promoter is not always optimally active. An inducible promoter is capable of directly or indirectly activating transcription of one or more DNA sequences or genes in response to an inducer. Some inducible promoters are activated by physical means such as the heat shock promoter ("Hsp"). Others are activated by a chemical, for example, IPTG or tetracycline ("Tet on" system). Other examples of inducible promoters include the metallothionine promoter, which is activated by heavy metal ions, and hormone-responsive promoters, which are activated by treatment of certain hormones. In the absence of an inducer, the nucleic acid sequences or genes under the control of the inducible promoter will not be transcribed or will only be minimally transcribed. When any plasmids of the present invention contain an inducible promoter, the method of the present invention further includes the step of adding an appropriate inducing agent to the cell culture of the first and second cells when activation of the promoter is desired.

Also suitable for use in the present invention is the inclusion of a repressible promoter for temporal control of gene expression. A repressible promoter here is an operational term describing a promoter whose activity can be repressed by the presence of an environmental cue (e.g., a "repressing agent"), with the removal of such a cue resulting in the activation of the promoter. An example of such a regulating system is the "Tet off" expression system. Therefore, when a repressible promoter is included in the third and fourth plasmids, this aspect of the present invention further includes adding an appropriate repressing agent to the cell culture of the first and second cells either prior to, or immediately following, transfection with the plasmid having a repressible promoter, and then removing the repressing agent when appropriate gene expression is desired.

In this aspect of the present invention, the DBD-TP expression unit in the first plasmid is preferably under control of a constitutive promoter and the DBS-controlled reporter expression unit in the second plasmid preferably includes a minimal 5' promoter element for low level basal activity. Examples of such minimal promoters include the ΔMTV promoter derived from mouse mammary tumor virus, the ΔSV promoter derived from the SV40 virus early promoter, the thymidine kinase (tk) promoter and/or its derivatives from the herpes simplex virus, any suitable cellular basal promoter with the enhancer(s) removed, as well as any artificially constructed basal promoter such as that composed of the basal "TATA" element. The ACT-PMP and ACT-PMPmut expression units in the third and fourth plasmids in this aspect of the present invention may be under control of a constitutive promoter, an inducible promoter, or a repressible promoter, as described above. Because the fourth plasmid functions as a control for the third plasmid, it is preferable that the fourth plasmid have the same type of promoter as the third in any given assay.

All plasmids of the present invention also include operable 3' regulatory elements, selected from among those elements which are capable of providing correct transcriptional termination and proper polyadenylation of mRNA for expression in the host cell of choice, operably linked to a DNA molecule which encodes a protein of choice. Exemplary 3' regulatory elements include, without limitation, the nopaline synthase ("nos") 3' regulatory region (Fraley, et al., "Expression of Bacterial Genes in Plant Cells," *Proc. Nat'l Acad. Sci. USA* 80(15):4803–4807 (1983), which is hereby incorporated by reference in its entirety) and the cauliflower mosaic virus ("CaMV") 3' regulatory region (Odell, et al., "Identification of DNA Sequences Required for Activity of the Cauliflower Mosaic Virus $^{35}$S Promoter," *Nature* 313 (6005):810–812 (1985), which is hereby incorporated by reference in its entirety). An example of a commonly-used 3' regulatory element for expression of genes of interest in mammalian cells is the SV40 polyadenylation signal derived from the SV40 virus. Virtually any 3' regulatory element known to be operable in the host cell of choice will suffice for proper expression of the genes contained in the plasmids of the present invention.

A vector of choice, a suitable promoter, nucleic acid molecules specific to each plasmid as described above, an appropriate 3' regulatory region, as well as other regulatory element(s) if appropriate, can be used to construct the four expression plasmids of the first aspect of the present invention, using well known molecular cloning techniques in the art, such as those described in Sambrook et al., *Molecular Cloning: A Laboratory Manual*, Second Edition, Cold Spring Harbor Press, N.Y. (1989), and Ausubel et al., *Current Protocols in Molecular Biology*, John Wiley & Sons, New York, N.Y. (1989), which are hereby incorporated by reference in their entirety. Once constructed, the plasmids of this aspect of the present invention can be amplified by propagation in a suitable host cell (e.g., in *E. coli*) and subsequently produced in a larger quantity. Methods of producing plasmids in desired quality and quantity are well known in the art.

Once an expression plasmid construct of the present invention has been prepared in sufficient quality and quantity, it is ready to be incorporated into a suitable host cell to practice the method described in this aspect of the present invention. Basically, this is carried out by transforming or transfecting a host cell with a plasmid of the present invention, using standard procedures known in the art, such as described by Sambrook et al., *Molecular Cloning: A Laboratory Manual*, Second Edition, Cold Spring Harbor Press, N.Y. (1989), which is hereby incorporated by reference in its entirety. Suitable host cells for the present invention include, without limitation, yeast cells, mammalian cells, including human cells, as well as any other cell system that is suitable for examining modification of a TP by a PMP. Methods of transformation or transfection may result in transient or stable expression of the genes of interest contained in the plasmids. Transient expression by the host cells of the present invention is sufficient for carrying out the present invention, although stable expression is also suitable. Stable expression of some or all of the components of the present invention would be more desirable in certain applications contained in later part of the present invention, such as the method and the kit for screening compounds modulating the modification of a TP by a PMP, the method for large-scale detection of candidate target proteins of a PMP, and the cell-based assay kit for determining whether a test protein is modified by a PMP. Methods of transforming yeast cells and transfecting mammalian cells are well known in the art. Examples of suitable methods for transfecting mammalian cells include, without limitation, calcium phosphate coprecipitation, electroporation, and lipofection. Following transformation or transfection, the cells are then cultured in a suitable way as per the specific cell type, the desired expression (transient vs. stable), and the nature of the reporter whose activity is going to be assayed.

In the case when a stable expression of a gene of interest is desired, stably transfected cells can be identified using a selection marker simultaneously introduced into the host cells along with the plasmid construct of the present invention. Usually, the selection marker is contained in the plasmid. Suitable selection markers include, without limitation, markers encoding for antibiotic resistance, such as the neomycin resistance gene and the hygromycin resistance gene (Southern and Berg, "Transformation of Mammalian Cells to Antibiotic Resistance With a Bacterial Gene Under the Control of the SV40 Early Region Promoter," *J Mol Appl Genet.*, 1(4):327–41 (1982); Bernard et al., "Construction of a Fusion Gene That Confers Resistance Against Hygromycin B to Mammalian Cells in Culture," *Exp Cell Res.* 158(1):237–43 (1985), which are hereby incorporated by reference in their entirety).

The present invention also relates to a method for screening a candidate protein for E3 ligase activity. This involves providing a first cell containing: a first plasmid having an expression unit with a first nucleic acid molecule encoding a DNA binding domain operably linked to a second nucleic acid molecule encoding a target protein, where the expression of the DBD and TP in the cell produces a DBD-TP fusion protein; a second plasmid having an expression unit with a first nucleic acid molecule encoding a reporter protein operably linked to a second nucleic acid molecule encoding a DNA binding site ("DBS") to which the DNA binding domain of the DBD-TP fusion protein of the first plasmid is capable of binding, with expression of the reporter protein under the control of the DBS; a third plasmid having an expression unit with a first nucleic acid molecule encoding an ACT operably linked to a second nucleic acid molecule encoding a known or suspected PMP, and expression of the ACT and PMP in the cell produces a ACT-PMP fusion protein; and a fourth plasmid having a nucleic acid molecule encoding a candidate E3 ligase. This method also involves providing a second cell containing the first, second, and third plasmids, and a fifth plasmid. The fifth plasmid has an expression unit having no nucleic acid molecule insert. The first and second cells are cultured under conditions effective for post-translational modification of the target protein to occur. Reporter activity is determined in the first and second cells. An increase in reporter activity in the first cell compared to the second cell indicates that the candidate E3 ligase has E3 ligase activity.

Figure 3A:
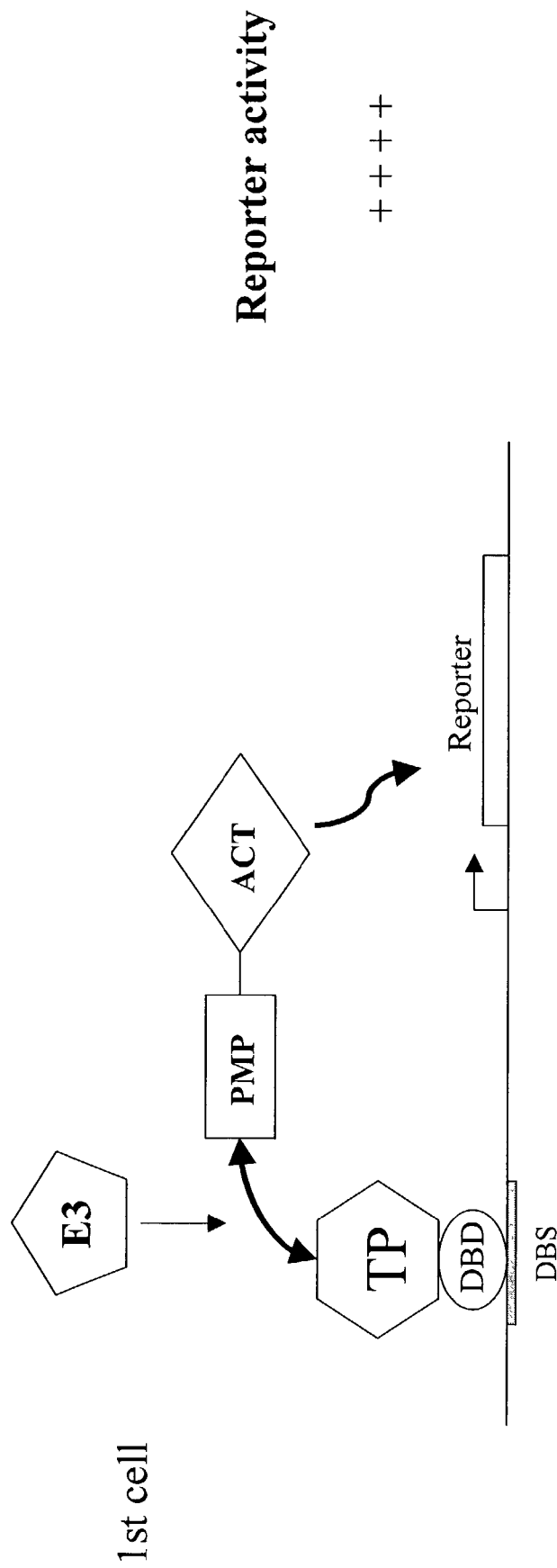
FIGS. 3A–D are schematic drawings showing the testing of a candidate protein for E3 ligase activity.
Figure 3B:
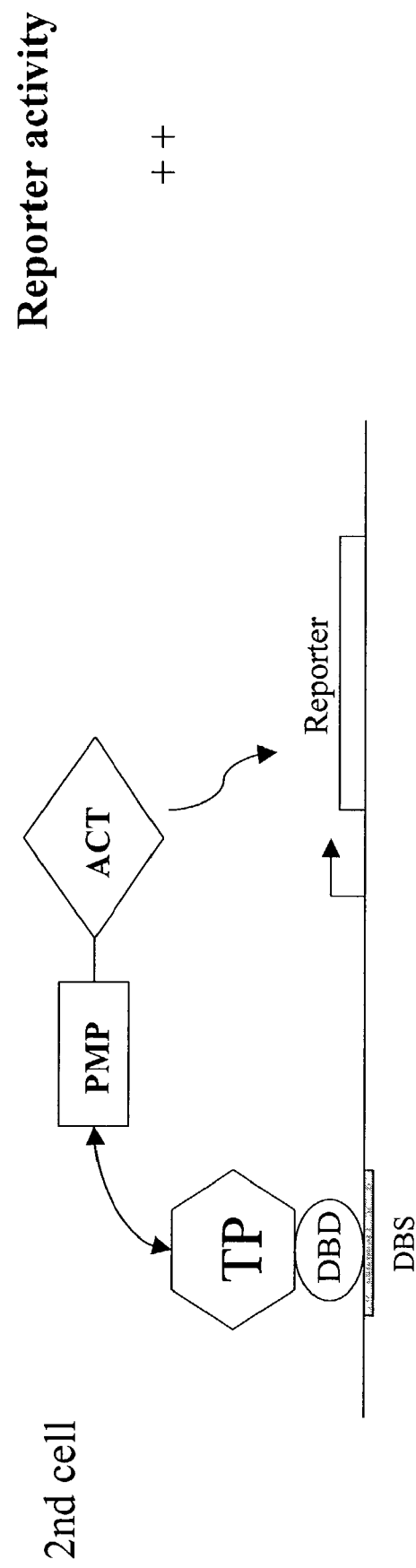

FIGS. 3A–B illustrate this aspect of the present invention. Because the PMP expressed from the third plasmid is known to covalently attach to the TP molecule expressed from the first plasmid, reporter activity is expected in both the first and the second cells, due to the formation of a covalent complex (DBD-TP-PMP-ACT), as shown in FIG. 3A and FIG. 3B, which places the reporter gene under the control of the ACT moiety of ACT-PMP fusion protein expressed from the third plasmid. However, there is an up-regulation of the reporter protein expression in the first cell compared to the reporter activity of the second cell if the candidate E3 molecule, shown as "E3" in FIG. 3A, encoded in the fourth plasmid, functions as an E3 ligase in the cell. This increase in reporter activity is due to the function of the exogenously expressed E3. Without wishing to be limited to a specific explanation, it is thought that the E3 ligase is an important enzyme in the reaction cascade that results in the conjugation of the PMP to the TP expressed from the first plasmid. The presence of the excess E3 in the first cell compared to the physiologically available level in the second cell further stimulates the modification of TP by the PMP, resulting in the increased production of the covalent complex shown in FIG. 3A. This results in an enhanced expression of the reporter protein in the first cell, compared to the second cell, which is shown in FIG. 3B.

This aspect of the present invention also relates to providing a third cell transfected with the first, second, and fourth plasmids of this aspect of the present invention, and also with a sixth plasmid. The sixth plasmid contains an expression unit having a first nucleic acid molecule encoding the same transcription activation domain that is encoded in the third plasmid, operably linked to a second nucleic acid molecule encoding a PMPmut mutant form of the PMP of the third plasmid that is defective or deficient in effecting post-translational modification of the target protein, wherein expression of the ACT and PMPmut in cells produces a ACT-PMPmut fusion protein. This further involves providing a fourth cell transfected with the first, second, fifth, and sixth plasmids, and determining the reporter activity in the third and fourth cells. The reporter activity of the third cell is subtracted from the reporter activity of the first cell to generate a first normalized reporter activity. The reporter activity of the fourth cell is subtracted from the reporter activity of the second cell to generate a second normalized reporter activity. The first normalized reporter activity is compared with the second normalized reporter activity, and an increase in reporter activity in the first normalized reporter activity compared with the second normalized reporter activity indicates that the candidate E3 ligase has E3 ligase activity.

In this aspect of the present invention, suitable post-translational modifier polypeptide molecules, DNA binding domains, DNA binding sites, transcription activation domains, and reporter proteins are as described above, with the exception of the target protein. In contrast to the first aspect of the present invention, suitable target proteins in this aspect are those that are known or suspected to be modified by a particular PMP. Therefore, the TP in this aspect of the present invention is chosen with the selected PMP in mind. Plasmid preparation is also carried out as described above, including the choice of suitable vectors, 5' and 3' regulatory regions, other regulatory element(s) when appropriate, host cells, as well as necessary methodology available in the art. In this aspect, the DBD-TP expression unit in the first plasmid is preferably under the control of a constitutive promoter. The DBS-controlled reporter expression unit in the second plasmid preferably includes a minimal 5' promoter element for low level basal activity. The ACT-PMP and ACT-PMPmut expression units in the third and sixth plasmids, and the candidate E3 expression unit in the fourth plasmid in this aspect of the present invention may be under control of a constitutive promoter, an inducible promoter, or a repressible promoter, as described above. Because the fifth plasmid functions as a control for the fourth plasmid, it is preferable that the fifth plasmid have the same type of promoter as the fourth in any given assay. For a similar reason, the third and sixth plasmids preferably contain the same type of promoter for a given assay. When inducible or repressible promoters are selected, this aspect of the present invention also involves treating the cells or cell culture with an appropriate inducing agent(s) when expression of appropriate component(s) is desired, or the treatment with a repressing agent(s) as appropriate, with removal of the agent when expression of appropriate component(s) is desired. In this aspect of the present invention, host cells are selected from the group consisting of, but not limited to, yeast cells, mammalian cells, including human cells, as well as any other cell system that is suitable for examining modification of a TP by a PMP.

Figure 3C:
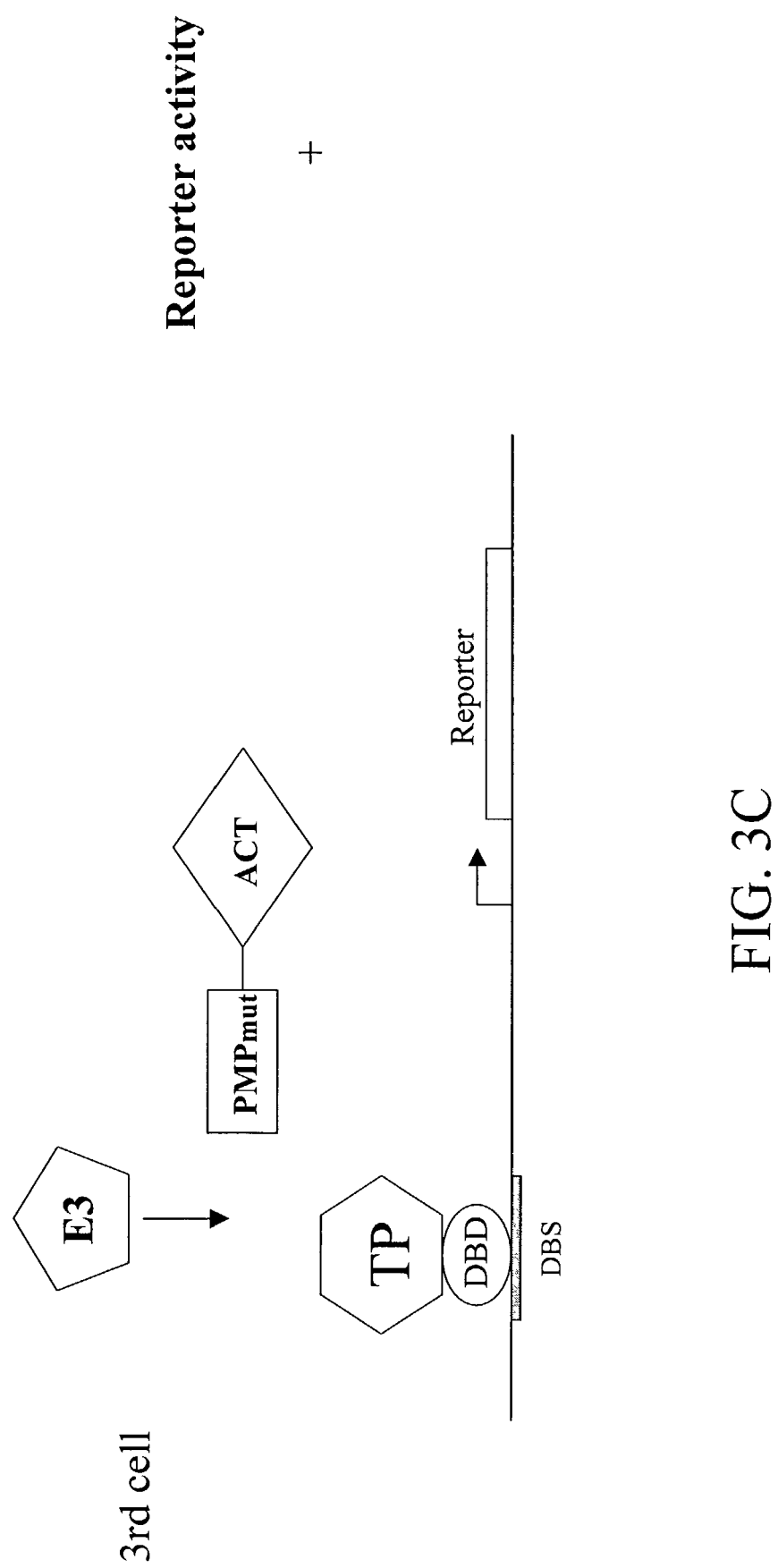

As shown in FIG. 3C, the third cell in this aspect of the present invention serves as a control, having a null PMP molecule in the sixth plasmid. The reporter activity in the third cell is determined and is subtracted from the reporter activity of the first cell to generate a first normalized reporter activity for the assay.

Figure 3D:
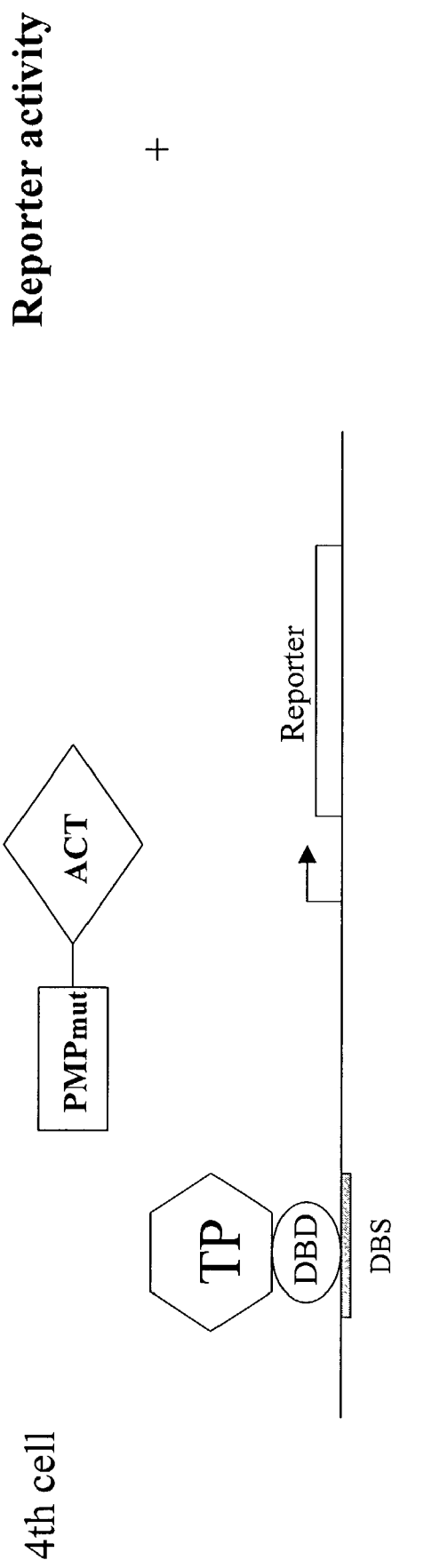

This aspect of the present invention also involves providing a fourth cell transfected with the first, second, fifth, and sixth plasmids as described above. Reporter activity in the fourth cell is determined, and the activity measured is subtracted from the activity measured in the second cell to generate a second normalized reporter activity. As shown in FIG. 3D, reporter activity is expected to be minimal in the fourth cell, because the mutant post-translational modifier polypeptide molecule ("PMPmut" in FIG. 3D) is unable to covalently attach to the target protein, and the reporter remains under the control of only a minimal promoter. The first and second normalized reporter activities are also compared. An increase in reporter activity in the first normalized reporter activity compared with the second normalized reporter activity indicates that the candidate E3 protein expressed from the fourth plasmid has E3 ligase activity.

The present invention also relates to a method of screening a test compound for the ability to regulate the post-translational modification of a TP by a PMP molecule. This method involves providing first and second cells containing: a first plasmid having an expression unit with a first nucleic acid molecule encoding a DBD that is operably linked to a second nucleic acid molecule encoding a TP, wherein expression of the DBD and TP in the cells produces a DBD-TP fusion protein; a second plasmid having an expression unit with a first nucleic acid molecule encoding a first reporter protein that is operably linked to a second nucleic acid molecule encoding a DBS to which the DBD of the DBD-TP fusion protein is capable of binding, and where expression of the reporter protein is under the control of the DBS; and a third plasmid having an expression unit with a first nucleic acid molecule encoding an ACT operably linked to a second nucleic acid molecule encoding a PMP capable of effecting post-translation modification of the TP, where expression of the ACT and PMP in the cells produces an ACT-PMP fusion protein. The first and second cells are cultured under conditions effective for post-translational modification of the TP to occur. The first cell is contacted with a test compound under conditions effective to allow the regulation of post-translational modification of the target protein to occur. The activity of the reporter in the first and second cells is determined. The activity of the first reporter in the first cell is normalized for non-specific effect of the test compound (as described below), and a change in reporter activity in the first cell compared to the second cell, after normalizing, indicates that the test compound regulates the post-translational modification of the TP by the PMP.

In this third aspect of the present invention, the first, second, and third expression plasmids are prepared in a way similar to that described herein for the first, second, and third plasmids of the second aspect of the present invention. Therefore, in this third aspect of the present invention, suitable post-translational modifier polypeptide molecules, DNA binding domains, DNA binding sites, transcription activation domains, and reporter proteins are as described above for the second aspect of the present invention. Suitable target proteins in this third aspect of the present invention are those that are known or suspected to be modified by a particular post-translational modifier polypeptide molecule. Therefore, the TP is chosen with a corresponding PMP in mind. As in the second aspect of the present invention, plasmid preparation in this third aspect of the present invention is carried out as described above herein, including the choice of suitable vectors, 5' and 3' regulatory regions, other appropriate regulatory element(s), host cells, as well as necessary methodology available in the art. Here, the DBD-TP expression unit in the first plasmid is preferably under the control of a constitutive promoter. The DBS-controlled reporter expression unit in the second plasmid preferably includes a minimal 5' promoter element for low level basal activity. The ACT-PMP expression unit in the third plasmid may be under control of a constitutive promoter, an inducible promoter, or a repressible promoter, as described above. When inducible or repressible promoters are selected, this aspect of the present invention also involves treating the cells or cell culture with an appropriate inducing agent(s) when expression of appropriate component(s) is desired, or the treatment with a repressing agent(s) as appropriate, with removal of the agent when expression of appropriate component(s) is desired. In this aspect of the present invention, host cells are selected from the group consisting of, but not limited to, yeast cells, mammalian cells, including human cells, as well as any other cell system that is suitable for examining modification of a TP by a PMP.

The test compound may be a compound that either enhances or inhibits the post-translational modification of the target protein by the modifier polypeptide molecule. The effect of the compound is determined by the difference in reporter activity between the first cell and the second cell following contacting of the first cell with the test compound. The test compound may be added to the first cell in culture at various times. For example, when the ACT-PMP expression unit in the third plasmid is under the control of an inducible promoter, the test compound may be added to the first cell culture before, after, or at the same time as the addition of an inducing agent(s). When the ACT-PMP expression unit in the third plasmid is under the control of a repressible promoter, the test compound may be added before, after, or at the same time as a repressing agent(s) is removed.

Figure 4A:
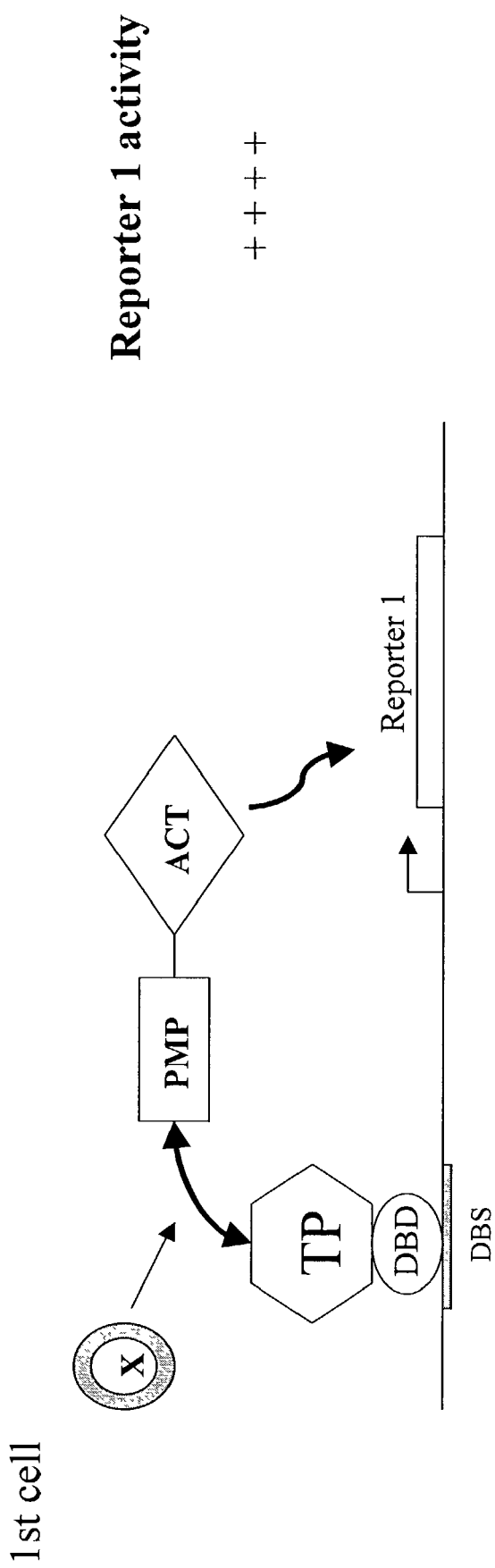
FIGS. 4A–B are schematic drawings showing the result of screening a test compound, "X," for its ability to regulate the post-translational modification of a TP.
Figure 4B:
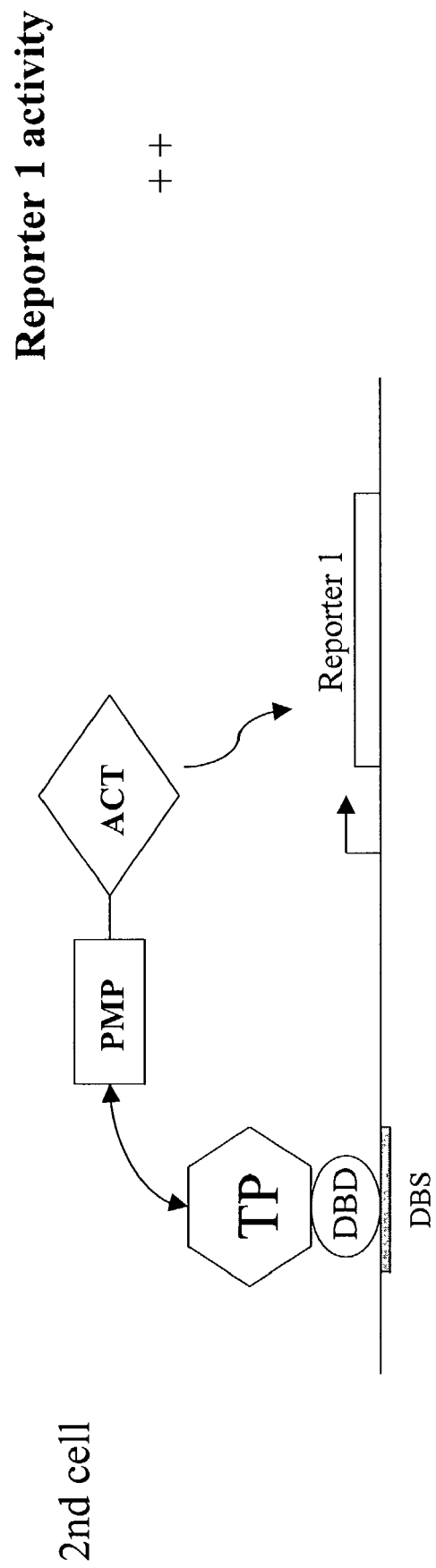

FIGS. 4A–B demonstrate the screening of a test compound, "X" for its ability to regulate the post-translational modification of a target protein. The first and second cells both contain a target protein that is capable of being post-translationally modified by the PMP expressed from the third plasmid in the respective cell, therefore both cells are expected to exhibit some measurable reporter activity. FIG. 4A shows that test compound "X" enhances the post-translational modification of the target protein (TP) by the modifier molecule (ACT-PMP) in the first cell, resulting in an up-regulation of reporter activity compared to FIG. 4B, which shows the second cell that contains the same plasmid components but is not contacted with the enhancer compound "X". The increase in reporter activity in FIG. 4A over that in FIG. 4B is attributable to the ability of compound "X" to enhance the post-translational modification of the TP by the PMP.

Figure 5A:
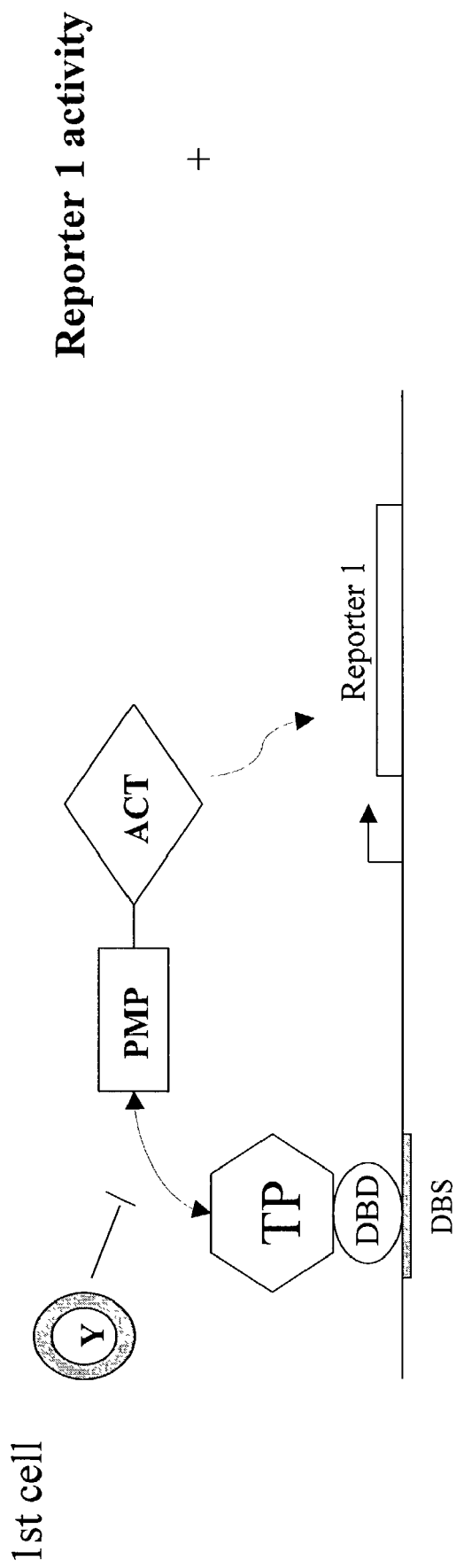
FIGS. 5A–B are schematic drawings showing the result of screening a test compound, "Y," for its ability to regulate the post-translational modification of a target protein.
Figure 5B:
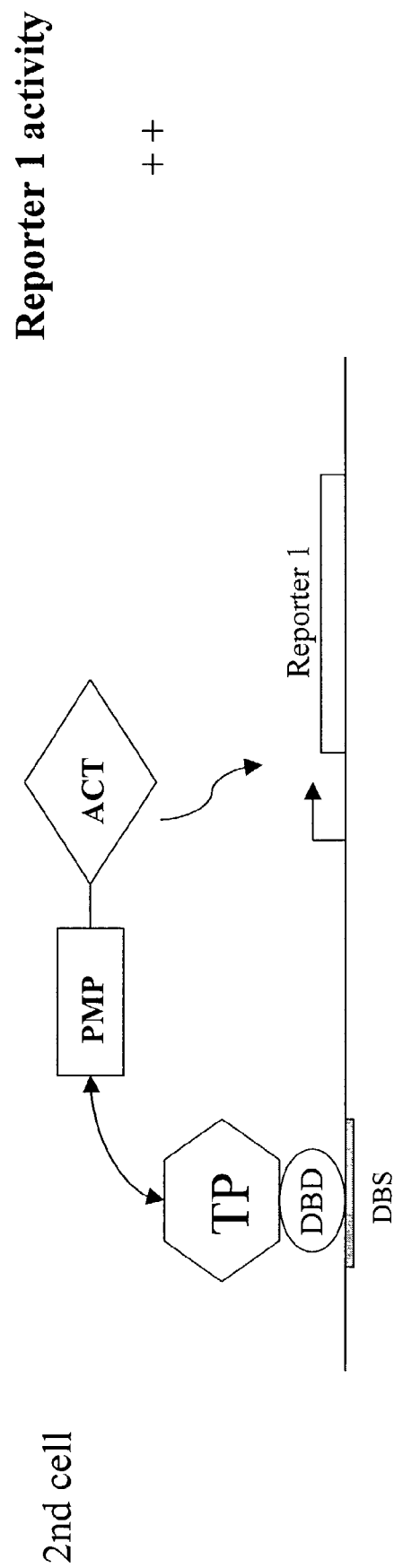

FIGS. 5A–B illustrate a test compound that reduces the modification of the target protein. Again, if not for the effect(s) of a test compound, the first cell and the second cell are both expected to exhibit measurable reporter activity because both cells contain a TP that is capable of being post-translationally modified by the PMP expressed from the third plasmid in the respective cell, which would place the reporter gene under the control of the ACT. The reporter activity in the second cell, as shown in FIG. 5B, exceeds the reporter activity of the first cell, shown in FIG. 5A. The test compound, shown as "Y" in FIG. 5A, has reduced the modification of TP by the PMP, resulting in lower expression of the reporter protein.

Figure 6A:
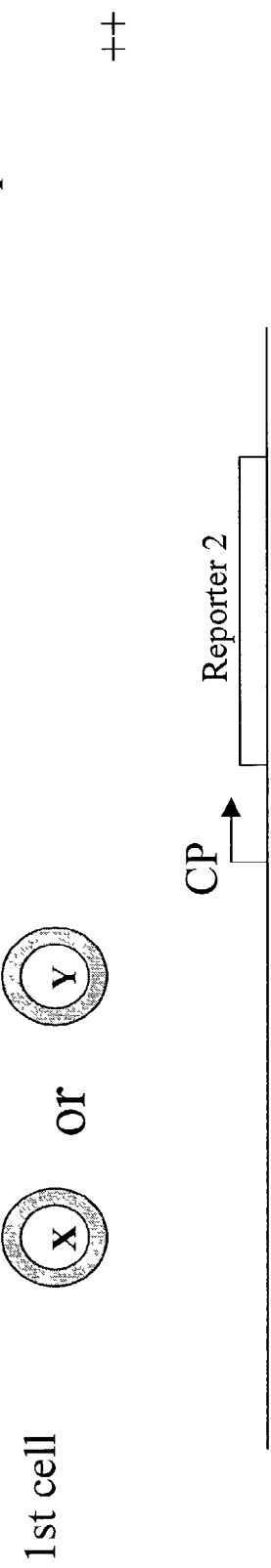
FIGS. 6A–B are schematic drawings showing the use of a fourth plasmid having a second reporter gene ("reporter 2") that is under the control of a constitutive promoter ("CP"), as an internal control.
Figure 6B:
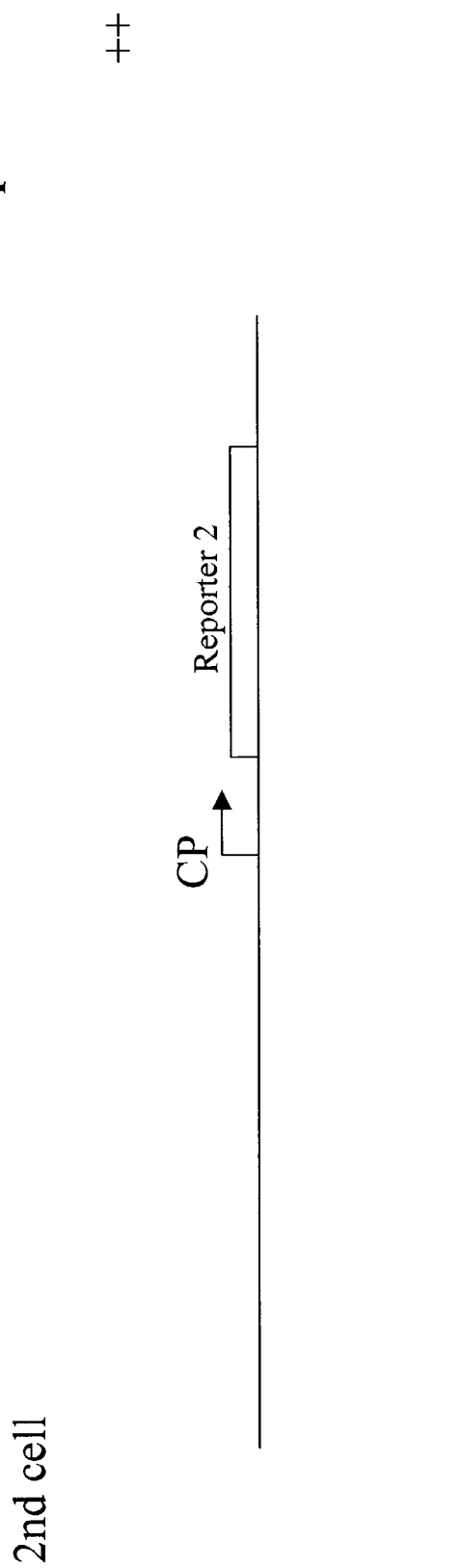

This aspect of the present invention also involves providing an internal control for nonspecific effect(s) on reporter activity by a compound. This involves providing a first and a second cell additionally transfected with a fourth plasmid. The fourth plasmid contains a nucleic acid molecule encoding a second reporter protein whose expression is under the control of a constitutive promoter, wherein the reporter protein encoded in the fourth plasmid can be readily distinguished from that encoded in the second plasmid by distinct reporter activity assays, even if both reporter proteins are to be present in one mixture, such as the lysate from cells simultaneously expressing both proteins. The second reporter protein is selected from the among those described above, or any other known reporters, so long as the reporter selected for the fourth plasmid can be readily distinguished from that encoded in the second plasmid by distinct reporter activity assays, even if both reporter proteins are to be present in one mixture, such as the lysate from cells simultaneously expressing both proteins. For convenience, the reporter selected for the second plasmid is referred here as reporter 1, while the reporter selected for the fourth plasmid is referred here as reporter 2. Any constitutive promoter capable of directing the expression a gene of interest in the host cell is operably linked to the nucleic acid molecule encoding reporter 2. The first and second cells are cultured as described above, and when applicable, the first cell is additionally contacted with a test compound as described above. The activities of both reporter 2 and reporter 1 in the first and second cells are determined. Any significant change of reporter 2 activity in the first cell compared to the second cell serves as an internal control for non-specific effect(s) that the test compound might exert on reporter activity in general in these cells. An example of such an internal control is illustrated in FIGS. 6A–B. Both the first cell, shown in FIG. 6A, and the second cell, shown in FIG. 6B, also express reporter 2. Unlike reporter 1, expression of reporter 2 is not controlled by the DBS, and thus, will not be affected by the post-translational modification of the DBD-TP fusion protein in cells. A test compound, X or Y, is added to the first cell, as shown in FIG. 6A, while no test compound is added to the control second cell, as shown in FIG. 6B. If a significant change in reporter 2 activity occurs in the first cell as compared to the second cell, the change in reporter 2 activity must be used to normalize any change in reporter 1 activity exhibited in the first cell compared to the second cell. In this way, any non-specific effect on reporter activity by a compound is taken into consideration, thus reducing the chance of generating false positives in the screening.

The present invention also relates to a method for the large-scale detection of candidate target proteins of post-translational modification by a modifier polypeptide molecule. This involves providing a cell system in a multiwell device, with the system having a plurality of first cells containing a first expression unit having a first nucleic acid molecule encoding a reporter protein operably linked to a second nucleic acid molecule encoding a DBS, wherein expression of the reporter protein is under the control of the DBS; and a second expression unit having a first nucleic acid molecule encoding an ACT operably linked to a second nucleic acid molecule encoding a known or suspected PMP, wherein expression of the ACT and PMP in the cells produces a ACT-PMP fusion protein. The cell system also contains a plurality of second cells containing the first expression unit and a third expression unit. The third expression unit has a first nucleic acid molecule encoding an ACT that is the same as that encoded by the second expression unit operably linked to a second nucleic acid molecule encoding a PMPmut of the first cell that is defective or deficient in effecting post-translational modification of target proteins, and expression of the ACT and PMPmut in the cells produces a ACT-PMPmut fusion protein. The first and second cells are placed into different wells of the multiwell device. Also provided is a plurality of additional expression units, each having a first nucleic acid molecule encoding a DBD operably linked to a second nucleic acid molecule encoding a candidate target protein ("CTP"), wherein the DBD is capable of binding to the DBS of the first expression unit of the cell system, and at least some of the plurality of these additional expression units contain genes encoding different CTPs. Furthermore, for at least some of the plurality of these additional expression units, expression of the DBD and CTP in the cells produces a DBD-CTP fusion protein. The first and second cells are transfected with the additional expression units. The first and second cells are cultured under conditions effective for post-translational modification to occur and reporter activity in each well in the multiwell system is measured. The reporter activity of the first cells is compared to the reporter activity of the second cells for each CTP. Post-translationally modified CTPs are identified as those that exhibit an increase in reporter activity in the first cells compared to the second cells.

In this fourth aspect of the present invention, suitable post-translational modifier polypeptide molecules, DNA binding domains, DNA binding sites, transcription activation domains, and reporter proteins are as described above for the first aspect of the present invention. Suitable candidate target proteins (CTPs) in this fourth aspect of the present invention are any proteins potentially capable of being modified by a particular post-translational modifier polypeptide molecule. Expression vector preparation is carried out as described above herein, including the choice of suitable vectors, 5' and 3' regulatory regions, other regulatory element(s) when appropriate, host cells, as well as necessary methodology available in the art. In this fourth aspect of the present invention, the first expression vector in both the first and second cells also preferably includes a minimal 5' promoter element for low level basal expression. The ACT-PMP and ACT-PMPmut expression units in the second and third expression vectors may be under the control of a constitutive promoter, or a repressible promoter, or an inducible promoter. In the plasmids containing the candidate target proteins, the DBD-CTP expression unit may be under the control of a constitutive, or a repressible promoter, or an inducible promoter. When any plasmids of this aspect of the present invention contain an inducible or repressible promoter, the cells or cell culture may be treated with an appropriate inducing agent(s) when expression of appropriate component(s) is desired, or with a repressing agent(s) as appropriate, with removal of the agent when expression of appropriate component(s) is desired. After transfection, the cells are cultured under suitable conditions that allow for the expression of the ACT-PMP or ACT-PMPmut fusion protein, and the DBD-CTP fusion protein if applicable. When the CTP moiety of a DBD-CTP fusion protein is a suitable substrate for post-translational modification by the PMP molecule encoded in the second expression vector, the resulting modification of DBD-CTP by ACT-PMP in the first cell places the reporter gene under the control of the ACT moiety through the formation of and the DBS-binding by the DBD-CTP-PMP-ACT covalent complex, and reporter protein expression is up-regulated.

Figure 7A:
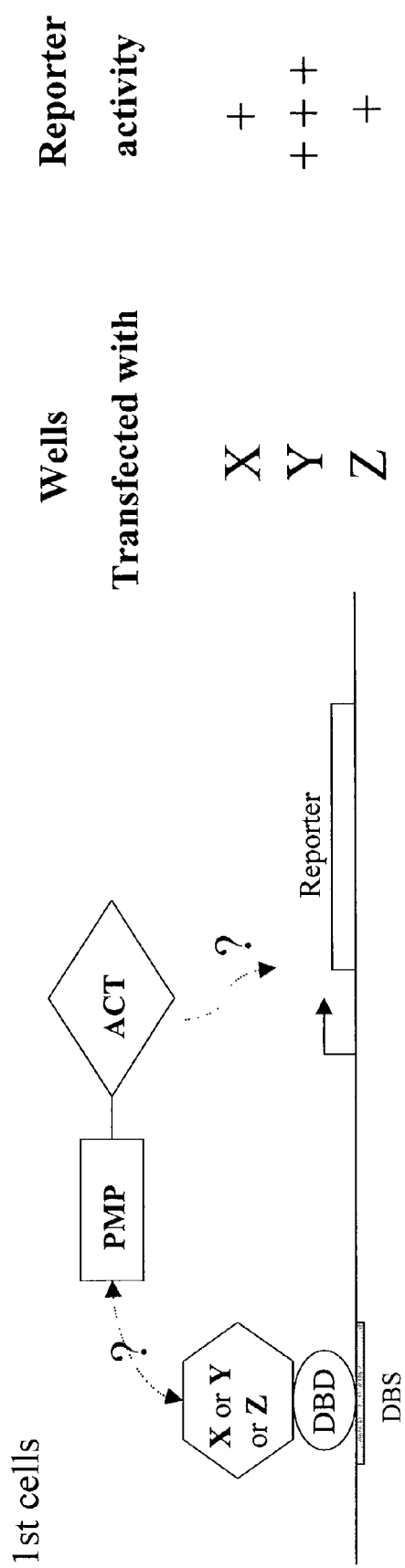
FIGS. 7A–B are schematic drawings showing the results of screening candidate target proteins "X," "Y," and "Z.
Figure 7B:
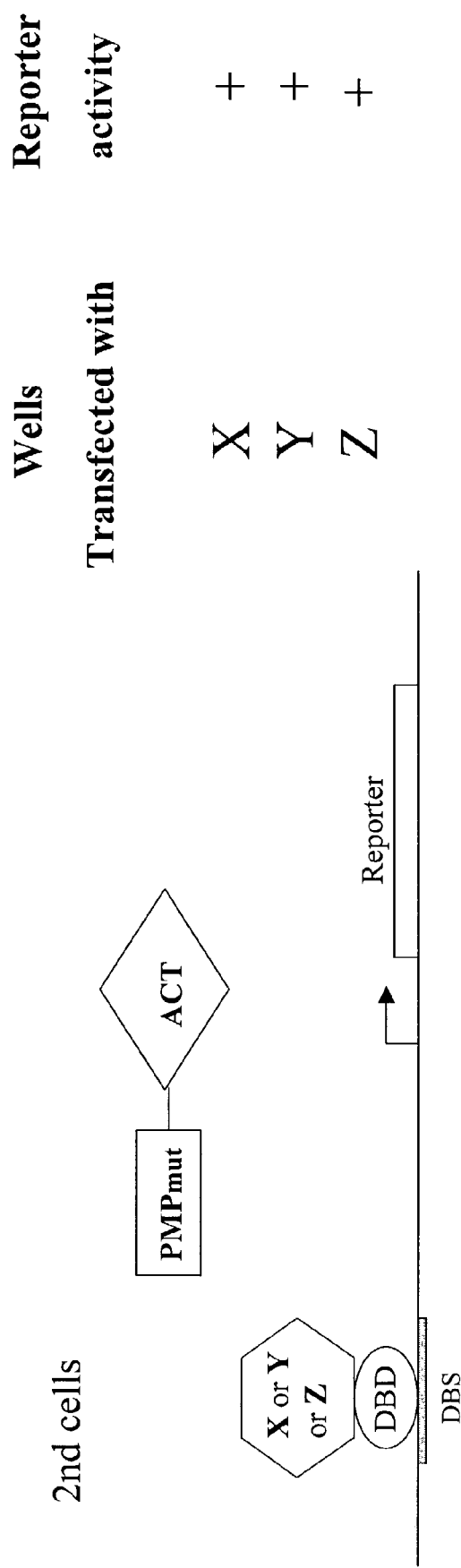

This fourth aspect of the present invention is shown in FIGS. 7A–B. As an example, three candidate target proteins, "X", "Y", and "Z", are shown in this illustration of screening. In FIGS. 7A and 7B, in the wells transfected with expression vectors containing candidate target proteins X and Z, both the first cells and the cognate second cells exhibit a similar extent of reporter activity (illustrated as "+"). In the wells transfected with the vector expressing candidate target protein Y, however, the first cell exhibits a greater reporter activity (illustrated as "+++") than the cognate second cell (illustrated as "+"). Since the second cells express the ACT-PMPmut that cannot carry out modification of target proteins, the reporter activity exhibited by the second cells is not attributed to the formation of the DBD-CTP-PMP-ACT covalent complex, instead, it serves as a control for nonspecific effect on reporter activity manifested by the DBD-CTP fusion protein itself. If a tested CTP (e.g., proteins X and Z in this illustration) exhibits similar extent of reporter activity in the first and second cells, it will be scored as negative (not modified) in this screening for modification by the PMP. On the other hand, if a tested CTP (e.g., protein Y in this illustration) exhibits an increase in reporter activity in the first cell as compared to the second cell, it will be scored as positive (modified) in this screening for modification by the PMP. Any multiwell device capable of being used for cell culture is suitable for this aspect of the present invention. This screening process is largely automatable, and thus providing a large-scale, quick through-put strategy for the identification of candidate proteins that are targets of modification by a given PMP. Systematic applications of this assay are appropriate for functional genomics and proteomics. Since post-translational modification of proteins plays important roles in modulating their functions, documentation of a modification pattern of the entire proteome would be a valuable part of the informatics of a cell. For example, the present invention can be scaled up to examine the sumolation pattern of the entire proteome (termed here as "sumolaome"). An engineered yeast system, in a scheme described above, can be used to systematically screen cDNAs/ORFs from a cell of interest for proteins that are sumolation targets. Similarly, the present invention can also be applied in a mammalian system for large scale screenings.

The present invention also relates to an assay kit for determining whether a test protein is post-translationally modified by a modifier polypeptide molecule. This kit includes a first plasmid which has an expression unit with a first nucleic acid molecule encoding a DBD, and which allows for a second nucleic acid molecule encoding a TP to be inserted so that expression of the DBD and TP in a cell produces a DBD-TP fusion protein. This kit also includes a second plasmid having an expression unit with a first nucleic acid molecule encoding a reporter protein operably linked to a second nucleic acid molecule encoding a DBS to which the DBD encoded in the first plasmid is capable of binding, and where expression of the reporter protein is under the control of the DBS. Also included in the kit is a third plasmid having an expression unit with a first nucleic acid molecule encoding an ACT operably linked to a second nucleic acid molecule encoding a PMP, wherein expression of the ACT and PMP in a cell produces a ACT-PMP fusion protein. A fourth plasmid is also included in the kit. The fourth plasmid has an expression unit with a first nucleic acid molecule encoding an ACT operably linked to a second nucleic acid molecule encoding a PMPmut that is defective or deficient in effecting post-translational modification of target proteins, where expression of the ACT and PMPmut in a cell produces a ACT-PMPmut fusion protein.

In addition, the kit may include a fifth and a sixth plasmid to serve as positive and negative controls for modification by the PMP. The fifth plasmid has a first nucleic acid molecule encoding the DBD that is the same as that encoded by the first plasmid, and a second nucleic acid molecule encoding a protein or polypeptide ("KT" for known target) that is known to be modified by the PMP, wherein expression of the DBD and KT in cells produces a DBD-KT fusion protein. The sixth plasmid is similar to the fifth plasmid, having an expression unit having a first nucleic acid molecule encoding the DNA binding domain encoded by the first plasmid, and a second nucleic acid that is a mutant form of KT of the fifth plasmid ("Ktmut") that can not be modified by the PMP.

In this aspect of the present invention, suitable post-translational modifier polypeptide molecules, DNA binding domains, DNA binding sites, transcription activation domains, and reporter proteins are as described above for the first aspect of the present invention, with the exception of the target protein. While the positive and negative control targets are supplied in the kit, the actual candidate target protein to be examined will be any protein selected for testing by the kit user. A nucleic acid encoding the selected target protein will be inserted into the first plasmid using standard cloning procedures, such as described in Sambrook et al., *Molecular Cloning: A Laboratory Manual,* Second Edition, Cold Spring Harbor Press, N.Y. (1989), and Ausubel, F. M. et al. (1989) *Current Protocols in Molecular Biology,* John Wiley & Sons, New York, N.Y., and U.S. Pat. No. 4,237,224 issued to Cohen and Boyer, which are hereby incorporated by reference in their entirety.

In this aspect of the present invention, the preparation of plasmids for inclusion in the kit is also carried out as described above herein, including the choice of suitable vectors, 5' and 3' regulatory regions, other regulatory element(s) when appropriate, host cells, as well as necessary methodology available in the art. In this aspect of the present invention, the DBD- or DBD-fusion protein expression units in the first, fifth, and sixth plasmids may be under the control of a constitutive promoter(s), the DBS-controlled reporter expression unit in the second plasmid preferably includes a minimal 5' promoter element for low level basal activity. The ACT-PMP and ACT-PMPmut expression units in the third and fourth plasmids in this aspect of the present invention may be under control of a constitutive promoter, an inducible promoter, or a repressible promoter, as described above. Because the fourth plasmid functions as a control for the third plasmid, it is preferable that the fourth plasmid have the same type of promoter as the third in any given assay. When inducible or repressible promoters are selected, this aspect of the present invention also involves treating cells containing cognate plasmid(s) with an appropriate inducing agent(s) when expression of appropriate component(s) is desired, or the treatment with a repressing agent(s) as appropriate, with removal of the agent when expression of appropriate component(s) is desired. In this aspect of the present invention, plasmids from this kit and that derived from this kit can be used to transform or transfect a variety of host cells to examine the potential modification of a test protein by the PMP. The choice of host cells is up to the user, which may include, but is not limited to, yeast cells, mammalian cells, including human cells, as well as any other cell system that is suitable for examining modification of a test protein by a PMP.

The present invention also relates to a kit for screening a test compound for the ability to regulate the post-translational modification of a TP by a PMP molecule. This kit contains a first cell having a first plasmid having a first nucleic acid molecule encoding a DBD operably linked to a second nucleic acid molecule encoding a TP, wherein expression of the DBD and TP in the cell produces a DBD-TP fusion protein. The first cell also contains a second plasmid having a first nucleic acid molecule encoding a first reporter protein operably linked to a second nucleic acid molecule encoding a DNA binding site to which the DBD of the DBD-TP fusion protein of the first plasmid is capable of binding, where expression of the first reporter protein is under the control of the DBS. The first cell also contains a third plasmid having a first nucleic acid molecule encoding an ACT operably linked to a second nucleic acid molecule encoding a PMP where expression of the ACT and PMP in the cell produces a ACT-PMP fusion protein.

In addition, the kit may contain a fourth plasmid included in the first cell to serve as an internal control. The fourth plasmid may contain a nucleic acid molecule encoding a second reporter protein ("reporter 2") whose expression is under the control of a constitutive promoter, wherein the reporter protein encoded in the fourth plasmid can be readily distinguished from that encoded in the second plasmid by distinct reporter activity assays, even if both reporter proteins are to be present in one mixture, such as the lysate from cells simultaneously expressing both proteins.

In this aspect of the present invention, suitable post-translational modifier polypeptide molecules, DNA binding domains, DNA binding sites, transcription activation domains, and reporter proteins are as described above for the first aspect of the present invention, with the exception of the target protein. Suitable target proteins in this aspect are those that are known or suspected to be modified by a particular PMP. Therefore, the TP in this aspect of the present invention is chosen with the selected PMP in mind.

In this aspect of the present invention, the preparation of plasmids for inclusion in the kit is also carried out as described above herein, including the choice of suitable vectors, 5' and 3' regulatory regions, other regulatory element(s) when appropriate, host cells, as well as necessary methodology available in the art. In this aspect of the present invention, the DBD-TP expression units in the first plasmid may be under the control of a constitutive promoter, the DBS-controlled reporter 1 expression unit in the second plasmid preferably includes a minimal 5' promoter element for low level basal activity. The ACT-PMP expression unit in the third plasmid in this aspect of the present invention may be under control of a constitutive promoter, an inducible promoter, or a repressible promoter, as described above. When an inducible or repressible promoter is selected, this aspect of the present invention also involves treating cells or cell culture with an appropriate inducing agent(s) when expression of ACT-PMP is desired, or the treatment with a repressing agent(s) as appropriate, with removal of the agent when expression of ACT-PMP is desired. The reporter 2 expression unit in the fourth plasmid is under the control of a constitutive promoter. In this aspect of the present invention, the choice of the first cell includes, but is not limited to, yeast cells, mammalian cells, including human cells, as well as any other cell system that is suitable for examining modification of a TP by a PMP.

The present invention also relates to an assay kit for determining whether a test protein is post-translationally modified by a modifier polypeptide molecule. This kit contains a first plasmid which has a first nucleic acid molecule encoding a DBD, and which allows for a second nucleic acid molecule encoding a TP to be inserted so that expression of the DBD and TP in a cell produces a DBD-TP fusion protein. Also provided is a first cell having a second plasmid with a first nucleic acid molecule encoding a reporter protein operably linked to a second nucleic acid molecule encoding a DBS to which the DBD encoded in the first plasmid is capable of binding, and where expression of the reporter protein is under the control of the DBS. The first cell also contains a third plasmid having a first nucleic acid molecule encoding an ACT operably linked to a second nucleic acid molecule encoding a PMP, where expression of the ACT and PMP in cells produces an ACT-PMP fusion protein. The kit also includes a second cell containing the second plasmid and a fourth plasmid. The fourth plasmid contains a first nucleic acid molecule encoding an ACT operably linked to a second nucleic acid molecule encoding a mutant form of the PMP of the third plasmid that is defective or deficient in effecting post-translational modification of a TP, wherein expression of the ACT and PMPmut in the cell produces a ACT-PMPmut fusion protein.

The kit may also include a fifth and a sixth plasmid to serve as positive and negative controls, respectively, for modification by the PMP. The fifth plasmid has a first nucleic acid molecule encoding a DBD that is the same as that encoded by the first plasmid, operably linked to a second nucleic acid molecule encoding a protein or polypeptide ("KT," for known target) that is the known to be modified by the PMP, where expression of the DBD and KT in cells produces a DBD-KT fusion protein. The sixth plasmid has a first nucleic acid molecule encoding the DBD of the first plasmid, operably linked to a second nucleic acid molecule encoding a mutant form of the known target protein or polypeptide of the fifth plasmid that cannot be modified ("Ktmut") by the PMP.

In this aspect of the present invention, suitable post-translational modifier polypeptide molecules, DNA binding domains, DNA binding sites, transcription activation domains, and reporter proteins are as described above for the first aspect of the present invention, with the exception of the target protein. While the positive and negative control targets are supplied in the kit, the actual candidate target protein to be examined will be any protein selected for testing by the kit user. A nucleic acid encoding the selected target protein will be inserted into the first plasmid using standard cloning procedures, such as described in Sambrook et al., *Molecular Cloning: A Laboratory Manual,* Second Edition, Cold Spring Harbor Press, N.Y. (1989), and Ausubel, F. M. et al. (1989) *Current Protocols in Molecular Biology,* John Wiley & Sons, New York, N.Y., and U.S. Pat. No. 4,237,224 issued to Cohen and Boyer, which are hereby incorporated by reference in their entirety.

In this aspect of the present invention, the preparation of plasmid for inclusion in the kit is also carried out as described above herein, including the choice of suitable vectors, 5' and 3' regulatory regions, other regulatory element(s) when appropriate, host cells, as well as necessary methodology available in the art. In this aspect of the present invention, the DBD- or DBD-fusion protein expression units in the first, fifth, and sixth plasmids may be under the control of a constitutive promoter(s), and the DBS-controlled reporter expression unit in the second plasmid preferably includes a minimal 5' promoter element for low level basal activity. The ACT-PMP and ACT-PMPmut expression units in the third and fourth plasmids in this aspect of the present invention may be under control of a constitutive promoter, an inducible promoter, or a repressible promoter, as described above. Because the fourth plasmid functions as a control for the third plasmid, it is preferable that the fourth plasmid have the same type of promoter as the third in any given assay. When inducible or repressible promoters are selected, this aspect of the present invention also involves treating cells containing cognate plasmid(s) with an appropriate inducing agent(s) when expression of appropriate component(s) is desired, or the treatment with a repressing agent(s) as appropriate, with removal of the agent when expression of appropriate component(s) is desired.

EXAMPLES

Example 1

Modification of Gal4-p53CT WT by VP-SUMO WT

To demonstrate the present invention, p53, a known SUMO target protein, was examined. The C-terminal portion of p53 ("p53CT WT") has been shown to be sufficient for sumolation, and contains a single SUMO-attachment site at K386. A single point mutation (K386R) that substitutes lysine 386 with arginine abolishes sumolation. Plasmids were constructed which express Gal4 fusions of the C-terminal portion of p53 ("Gal4-p53CT WT") as well as its non-modifiable mutant version ("Gal4-p53CT K386R"). Also constructed were plasmids expressing VP16-SUMO WT and VP16-SUMO GA. SUMO GA is identical to SUMO WT, except for a single point mutation (Gly 97 to Ala) that abolishes it ability to covalently modify target proteins.

Figure 8:
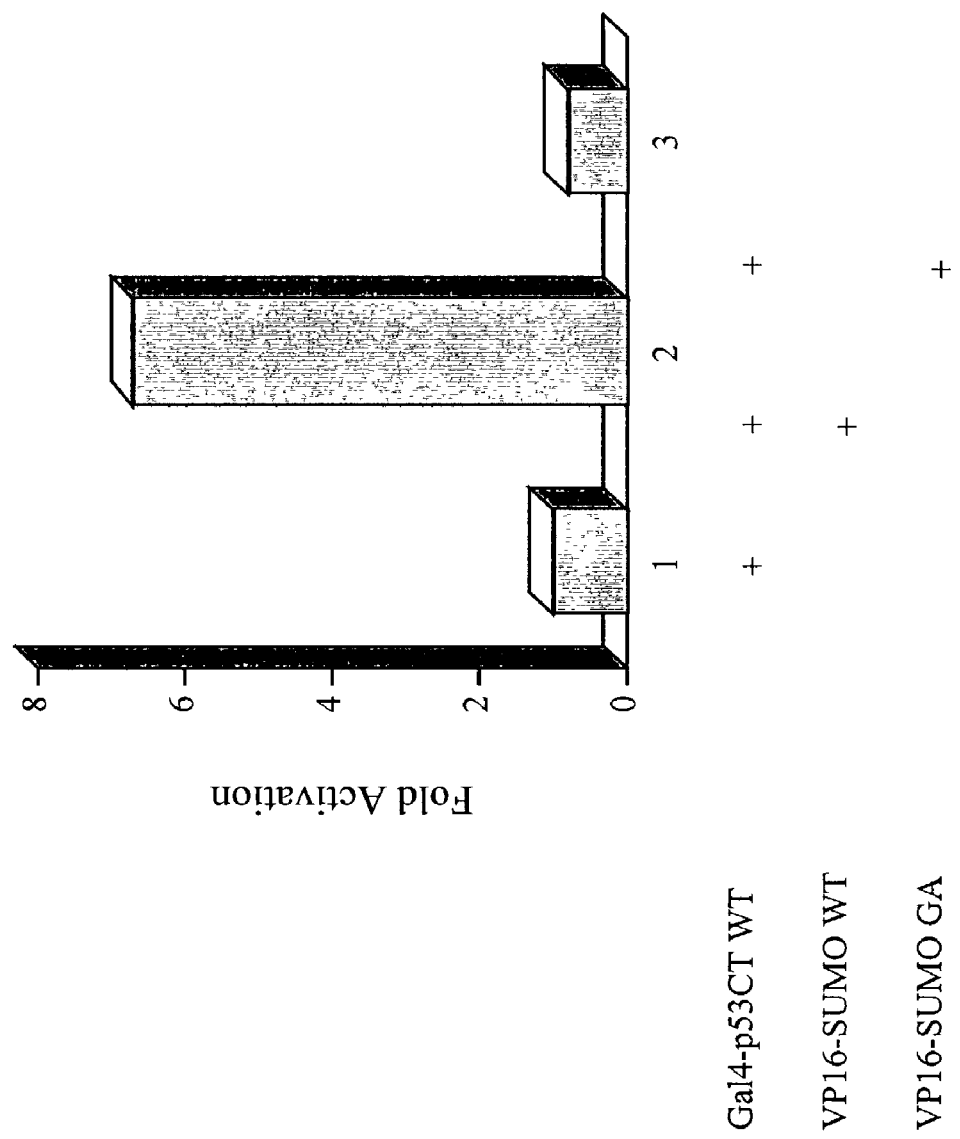
FIG. 8 shows the activation of the reporter gene in HeLa cells transfected with: a Gal4-reporter (G5-tk-CAT) and a plasmid expressing a wild-type p53 C-terminus target protein, fused to the Gal4 DBD (Gal4-p53CT WT), and a plasmid expressing a VP16 transactivation domain linked to either a functional wild-type SUMO modifier molecule ("SUMO WT") or a null SUMO modifier molecule ("SUMO GA").

HeLa cells were transfected with the Gal4-reporter G5-tk-CAT plasmid, and a plasmid expressing Gal4-p53CT WT, a fusion protein containing the Gal4 DNA binding domain and the last 100 amino acid residues of p53. This region has been shown to be sufficient for sumolation and contains the sumolation site K386. When appropriate, a plasmid expressing VP16-SUMO WT or VP16SUMO GA was cotransfected, as indicated in FIG. 8.

It was found that Gal4-p53CT WT and Gal4-p53CT K386R only slightly influenced the activity of the Gal4-reporter (in this case, G5-tk-CAT). As shown in FIG. 8, cotransfection of VP16-SUMO WT with Gal4-p53CT WT significantly activates the reporter (by about 6-fold), while no activation (compared to Gal4-p53CT WT background) is detected when the PMPmut molecule VP16-SUMO GA was used instead of the wild-type PMP molecule, VP16-SUMO WT. Fold activation was calculated by normalizing CAT activities to that of cells transfected with just the reporter and Gal4-p53CT WT.

Figure 9:
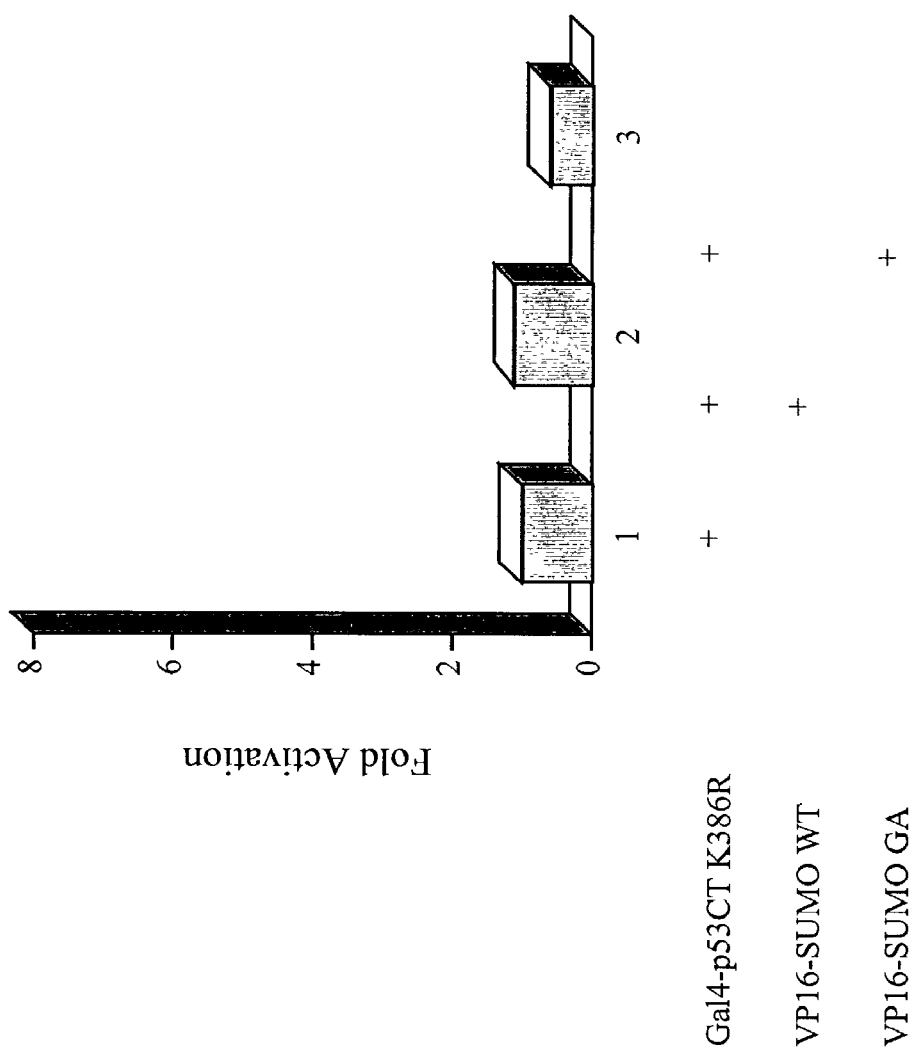
FIG. 9 shows the control for the experiment shown in FIG. 8. The target protein (wild type p53 C-terminus in FIG. 8) was substituted in the control experiment by a mutant, or "null," version ("p53CT K386R") that cannot undergo SUMO modification, resulting in only minimal reporter activation in cells containing either a functional wild-type SUMO modifier molecule ("SUMO WT") or a null SUMO modifier molecule ("SUMO GA").

This result confirms that the C-terminus of p53 was sumolated in the test cells. To further document that the observed reporter activation is due to sumolation of p53CT WT per se as opposed to other mechanisms, including a possible non-covalent association mechanism, a similar experiment was carried out using Gal4-p53CT K386R instead of Gal4-p53CT WT. As shown in FIG. 9, little or no activation of the reporter by either VP16-SUMO WT or VP16-SUMO GA was found. Taken together, these results demonstrated the specificity of present invention.

Example 2

Modification of Gal4-p53CT WT by VP-SUMO WT Examined in Another Cell Line

Figure 10:
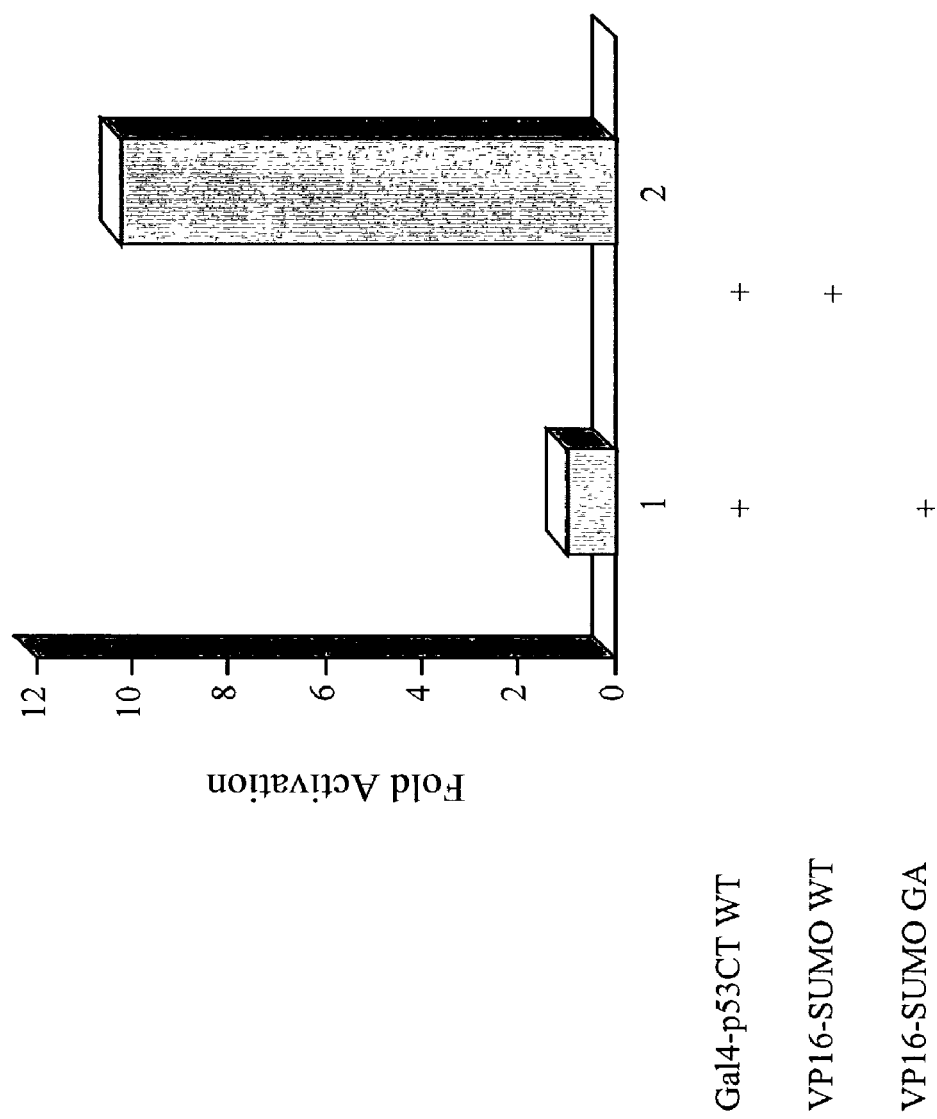
FIG. 10 shows the activation of the reporter gene in GH4C1 cells transfected with: a Gal4-reporter (G5-tk-CAT) and a plasmid expressing a wild-type p53 C-terminus fused to the Gal4 DBD (Gal4-p53CT WT), and either a plasmid expressing a VP16 transactivation domain linked to either a functional wild-type SUMO modifier molecule ("SUMO WT") or a null SUMO modifier molecule ("SUMO GA"). Reporter activity in the presence of VP16-SUMO GA is used to define 1-fold activation. Activation of the reporter by VP16-SUMO WT is compared to that by VP16-SUMO GA.
Figure 11:
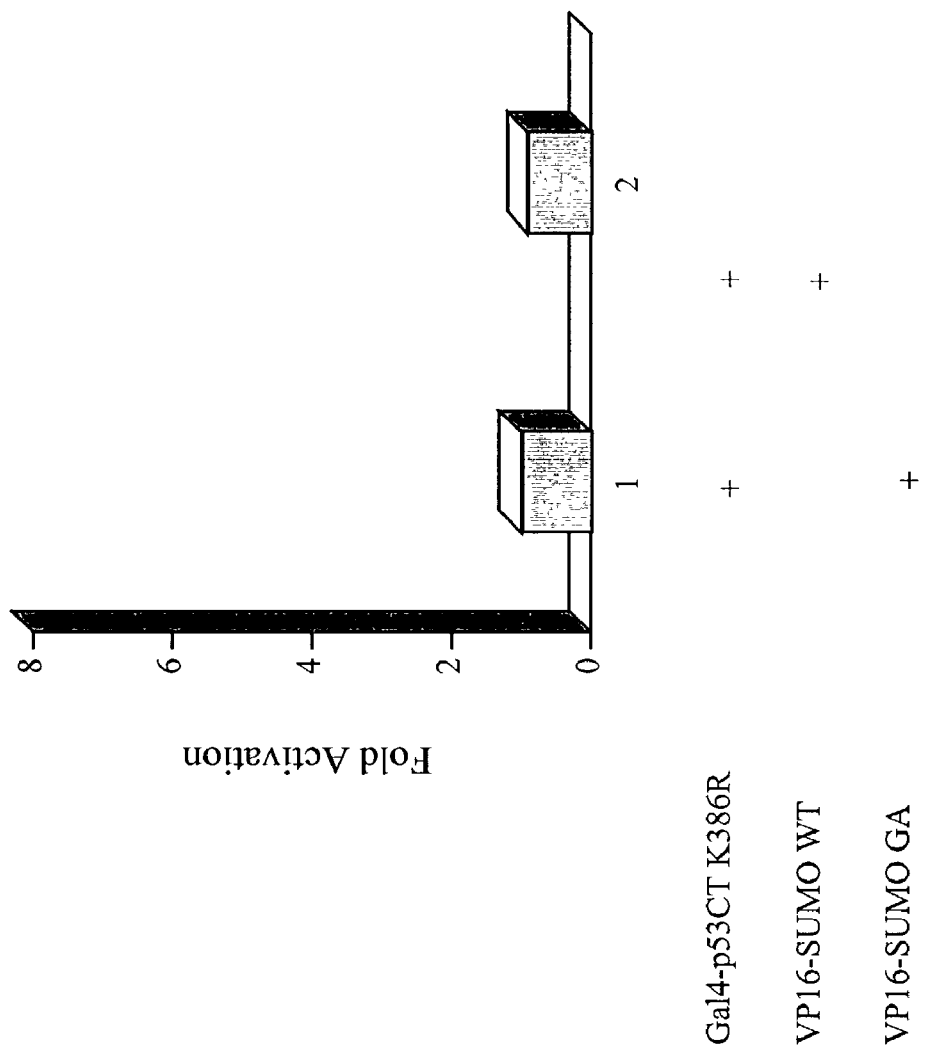
FIG. 11 shows the control for the experiment shown in FIG. 10. The target protein (wild type p53 C-terminus in FIG. 10) was substituted in the control experiment by a mutant version ("p53CT K386R") that cannot undergo SUMO modification, resulting in no further reporter activation in cells containing a functional wild-type SUMO modifier molecule ("SUMO WT") compared to cells containing a null SUMO modifier molecule ("SUMO GA").

To illustrate that the present invention can be applied to different types of cells, experiments were carried out similar to the specific example described above, but in a different cell line, GH4C1. GH4C1 cells were transfected with the Gal4-reporter G5-tk-CAT plasmid, and a plasmid expressing Gal4-p53CT WT. When appropriate, a plasmid expressing VP16-SUMO WT or VP16-SUMO GA was cotransfected, as indicated in FIG. 10. CAT activity in the presence of VP16-SUMO GA was used to define 1-fold activation. As shown in FIG. 10, cotransfection of VP16-SUMO WT with Gal4-p53CT WT results in a significant further activation of the reporter (by about 10-fold) comparing to cotransfection of VP16-SUMO GA, suggesting the sumolation of p53CT WT in GH4C1 cells. To further document that the observed reporter activation by VP16-SUMO WT is due to sumolation of p53CT WT per se as opposed to other mechanisms, including a possible non-covalent association mechanism, a similar experiment was carried out using Gal4-p53CT K386R instead of Gal4-p53CT WT. As shown in FIG. 11, in this case, cotransfection of VP16-SUMO WT results in no further activation of the reporter compared to cotransfection of VP16-SUMO GA. Thus, the successful demonstration of sumolation of p53CT WT in GH4C1 cells confirms the feasibility of applying the present invention in different types of cells.

Example 3

Modification of Gal4-p53FL WT by VP-SUMO WT

Figure 12:
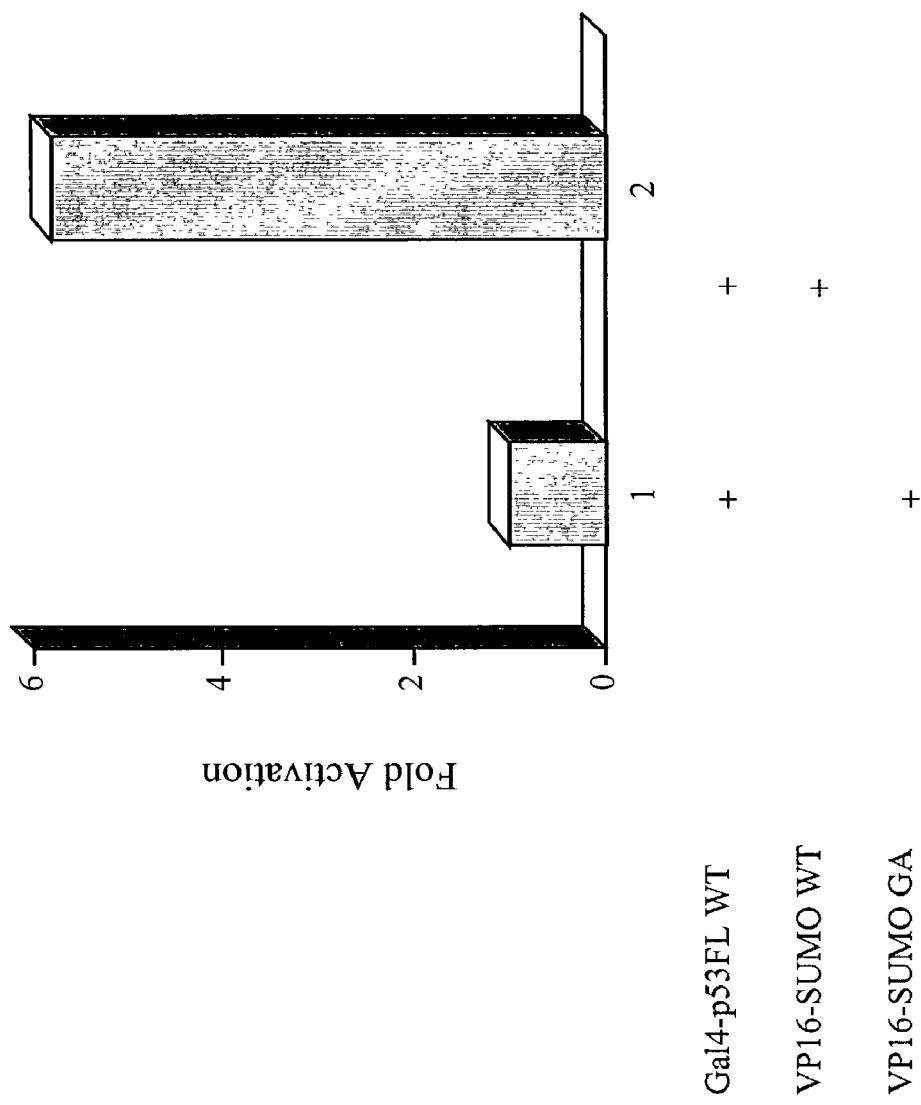
FIG. 12 shows the activation of the reporter gene in HeLa cells transfected with: a Gal4-reporter (G5-tk-CAT) and a plasmid expressing a wild-type full length p53 fused to the Gal4 DBD (Gal4-p53FL WT), and either a plasmid expressing a VP16 transactivation domain linked to either a functional wild-type SUMO modifier molecule ("SUMO WT") or a null SUMO modifier molecule ("SUMO GA"). Reporter activity in the presence of VP16-SUMO GA is used to define 1-fold activation. Activation of the reporter by VP16-SUMO WT is compared to that by VP16-SUMO GA.

The two examples shown above involve using p53CT WT as the test target protein for sumolation. It was found that Gal4-p53CT WT itself mediates little, if any, transcriptional activation in cells, which is an ideal trait for a candidate target protein that is to be examined. To illustrate that the present invention can also be applied to examine a candidate target protein that is itself transcriptionally active, experiments were performed with a full length wild-type p53 (p53FL WT). The full length wild-type p53 (p53FL WT) has also been shown to be a substrate for sumolation, and contains a single SUMO-attachment site at K386. A single point mutation (K386R) that substitutes lysine 386 with arginine abolishes sumolation. Plasmids were constructed which express Gal4 fusions of the full length wild-type p53 (Gal4-p53FL WT) as well as its non-modifiable mutant version (Gal4-p53FL K386R). HeLa cells were transfected with the Gal4-reporter G5-tk-CAT plasmid, and a plasmid expressing Gal4-p53FL WT. When appropriate, a plasmid expressing VP16-SUMO WT or VP16-SUMO GA was cotransfected, as indicated in FIG. 12.

Figure 13:
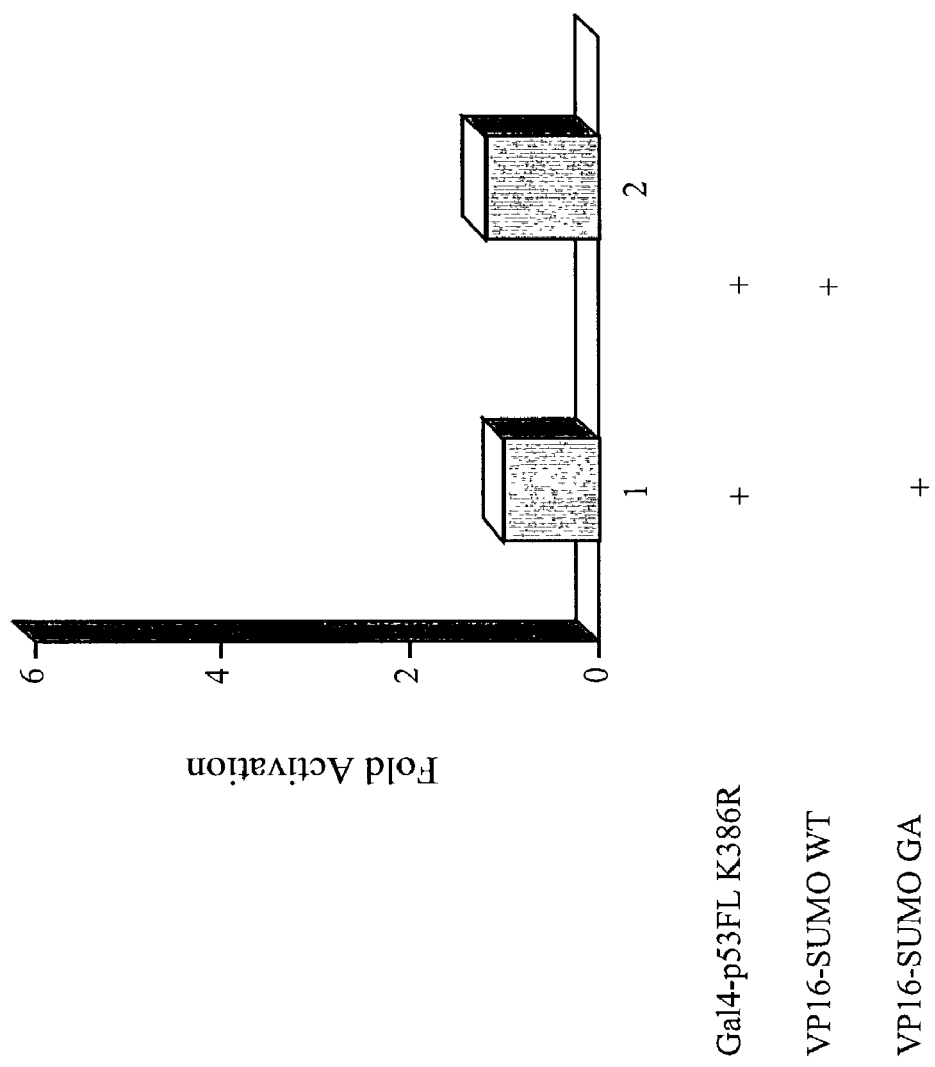
FIG. 13 shows the control for the experiment shown in FIG. 12. The target protein (wild type full length p53 FIG. 12) was substituted in the control experiment by a mutant version ("p53FL K386R") that cannot undergo SUMO modification, resulting in no further reporter activation in cells containing a functional wild-type SUMO modifier molecule ("SUMO WT") compared to cells containing a null SUMO modifier molecule ("SUMO GA").

It was found that although Gal4-p53FL WT itself mediates activation of the reporter, cotransfection of VP16-SUMO WT results in a significant further activation of the reporter (by about 6-fold) comparing with cotransfection of VP16-SUMO GA. This result is illustrated in FIG. 12, where the reporter activity in the presence of VP16-SUMO GA was used to define 1-fold activation. This result confirms that the full length wild-type p53 was sumolated in the test cells. To further document that the observed reporter activation is due to sumolation of p53FL WT per se as opposed to other mechanisms, including a possible non-covalent association mechanism, a similar experiment was carried out using Gal4-p53FL K386R instead of Gal4-p53FL WT. As shown in FIG. 13, in this case, cotransfection of VP16-SUMO WT results in no further activation of the reporter compared to cotransfection of VP16-SUMO GA. Thus, the successful demonstration of sumolation of a full length wild-type p53, which is itself transcriptionally active, confirms the feasibility of applying the present invention into examining candidate target proteins that are themselves not transcriptionally inert when fused to a DBD.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An assay method for detecting the post-translational modification of a target protein by a post-translational modifier polypeptide molecule comprising:
  providing a first cell containing:
    a first plasmid having an expression unit comprising a first nucleic acid molecule encoding a DNA binding domain operably linked to a second nucleic acid molecule encoding a target protein, wherein expression of the DNA binding domain and target protein in the cell produces a DNA binding domain-target protein fusion protein;
    a second plasmid having an expression unit comprising a first nucleic acid molecule encoding a reporter protein operably linked to a second nucleic acid molecule encoding a DNA binding site to which the DNA binding domain of the DNA binding domain-target protein fusion protein is capable of binding, and wherein expression of the reporter protein is under control of the DNA binding site; and a third plasmid having an expression unit comprising a first nucleic acid molecule encoding a transcription activation domain operably linked to a second nucleic acid molecule encoding a known or suspected post-translational modifier polypeptide, wherein expression of the transcription activation domain and post-translational modifier polypeptide in cells produces a transcription activation domain-post-translational modifier polypeptide fusion protein;

providing a second cell containing:

the first and second plasmids; and a fourth plasmid having an expression unit comprising a first nucleic acid molecule encoding a transcription activation domain operably linked to a second nucleic acid molecule encoding a mutant form of the post-translational modifier polypeptide that is defective or deficient in effecting post-translational modification of the target protein, wherein expression of the transcription activation domain and mutant post-translational modifier polypeptide in the cell produces a transcription activation domain-mutant post-translational modifier polypeptide fusion protein;

culturing the first and second cells under conditions effective for post-translational modification of the target protein to occur; and determining reporter activity in the first and second cells, where an increase in reporter activity in the first cell as compared to the second cell indicates that the target protein has undergone post-translational modification by the post-translational modifier polypeptide molecule.

2. The method according to claim 1, wherein the post-translational modifier polypeptide molecule is selected from the group consisting of a ubiquitin family protein, a SUMO family protein, a NEDD8 protein, and Apg12.

3. The method according to claim 1, wherein the DNA binding domain is a separable DNA binding domain of a transcriptional activator or repressor.

4. The method according to claim 1, wherein the transcription activation domain is a separable transcription activation domain from a transcriptional activator or other protein.

5. The method according to claim 1, wherein the reporter protein is selected from the group consisting of chloramphenicol acetyltransferase, luciferase, LacZ, green fluorescent protein, β-glucuronidase.

6. The method according to claim 1, wherein the target protein is a protein that is known or suspected to be modified by a post-translational modifier polypeptide.

7. The method according to claim 1, wherein the transcription activation domain-post-translational modifier polypeptide and the transcription activation domain-mutant post-translational modifier polypeptide expression units in the third and fourth plasmids are under control of a constitutive promoter.

8. The method according to claim 1, wherein the transcription activation domain-post-translational modifier polypeptide and the transcription activation domain-mutant post-translational modifier polypeptide expression units in the third and fourth plasmids are under control of an inducible promoter.

9. The method according to claim 1, wherein the transcription activation domain-post-translational modifier polypeptide and the transcription activation domain-mutant post-translational modifier polypeptide expression units in the third and fourth plasmids are under the control of a repressible promoter.

10. The method according to claim 1, wherein the first and second cells are selected from the group consisting of yeast cells, mammalian cells, and other cultured cells in which the post-translational modification of a target protein by a post-translational modifier polypeptide occurs.

11. The method according to claim 2, wherein the post-translational modifier polypeptide is a ubiquitin family protein.

12. The method according to claim 2, wherein the post-translational modifier polypeptide is a SUMO-family protein selected from the group consisting of SUMO-1, SUMO-2, SUMO-3.

13. The method according to claim 2, wherein the post-translational modifier polypeptide is a NEDD8 protein.

14. The method according to claim 2, wherein the post-translational modifier polypeptide is a Apg12 protein.

15. The method according to claim 3, wherein the DNA binding domain is a DNA binding domain of a Gal4 transcriptional activator or a DNA binding domain of a LexA transcriptional repressor.

16. The method according to claim 4, wherein the transcription activation domain is selected from the group consisting of VP16, B42, and an activation domain of Gal4.

17. The method according to claim 6, wherein the target protein is a target for modification by ubiquitin.

18. The method according to claim 6, wherein the target protein is a target for modification by a SUMO family protein.

19. The method according to claim 6, wherein the target protein is a target for modification by NEDD8.

20. The method according to claim 6, wherein the target protein is a target for modification by Apg12.

21. The method according to claim 18, wherein the target protein is selected from the group consisting of p53, p73, c-Jun, PML, Sp100, RanGAP1, RanBP2, Mdm2, and IkB.

22. The method according to claim 8, further comprising:
treating the cells containing the third or the fourth plasmid with an appropriate inducing agent to activate the inducible promoter.

23. The method according to claim 9 further comprising:
culturing the cells containing the third or the fourth plasmid with an appropriate repressing agent and removing the repressing agent when suitable to activate the repressible promoter.

24. The method according to claim 10, wherein the first and second cells are mammalian cells.

25. The method according to claim 10, wherein the first cell and second cells are yeast cells.

26. A method for the large-scale detection of candidate target proteins of post-translational modification by a modifier polypeptide molecule comprising:
providing a cell system in a multiwell device comprising:
a plurality of first cells containing a first expression unit having a first nucleic acid molecule encoding a reporter protein operably linked to a second nucleic acid molecule encoding a DNA binding site, wherein expression of the reporter protein is under control of the DNA-binding site; and a second expression unit having a first nucleic acid molecule encoding a transcription activation domain operably linked to a second nucleic acid molecule encoding a known or suspected post-translational modifier polypeptide, wherein expression of the transcription activation domain and the post-translational modifier polypeptide in the cells produces a transcription activation domain-post-translational modifier polypeptide fusion protein; and a plurality of second cells containing the first expression unit and a third expression unit having a first nucleic acid molecule encoding a transcription activation domain that is the same as that encoded by the second expression unit operably linked to a second nucleic acid molecule encoding a mutant form of the post-translational modifier polypeptide of the first cell, wherein the mutant post-translational modifier polypeptide is defective or deficient in effecting post-translational modification of a target protein, and wherein expression of the transcription activation domain and mutant post-translational modifier polypeptide in the cells produces a transcription activation domain-mutant post-translational modifier polypeptide fusion protein;

placing the first and second cells into different wells of the multiwell device;

providing a plurality of additional expression units each having a first nucleic acid molecule encoding a DNA binding domain operably linked to a second nucleic acid molecule encoding a candidate target protein, wherein the DNA binding domain is capable of binding to the DNA binding site of the first expression unit of the cell system, and wherein at least some of the plurality of additional expression units contain genes encoding different candidate target proteins, and wherein for at least some of the plurality of additional expression units, expression of the DNA binding domain and candidate target protein in the cells produces a DNA binding domain-candidate target protein fusion protein;

transfecting the first and second cells with the additional expression units;

culturing the first and second cells under conditions effective for post-translational modification to occur;

measuring reporter activity in each well in the multiwell system;

comparing reporter activity of the first cells to reporter activity of the second cells for each candidate target protein examined; and identifying as post-translationally modified those candidate target proteins that exhibit an increase in reporter activity in the first cells compared to the second cells.

27. The method according to claim 26, wherein the post-translational modifier is selected from the group consisting of a ubiquitin family protein, a SUMO family protein, a NEDD8 protein, and Apg12.

28. The method according to claim 26, wherein the reporter is selected from the group consisting of chloramphenicol acetyltransferase, luciferase, lacZ, green fluorescent protein, β-glucuronidase.

29. The method according to claim 26, wherein the DNA binding domain is a separable DNA binding domain of a transcriptional activator or repressor.

30. The method according to claim 26, wherein the transcription activation domain is a separable transcription activation domain from a transcriptional activator or other protein.

31. The method according to claim 26, wherein the transcription activation domain-post-translational modifier polypeptide expression unit of the first cell and the transcription activation domain-mutant post-translational modifier polypeptide expression unit of the second cell are under control of a constitutive promoter.

32. The method according to claim 26, wherein the transcription activation domain-post-translational modifier polypeptide expression unit in the first cell and the transcription activation domain-mutant post-translational modifier polypeptide expression unit in the second cell are under control of an inducible promoter.

33. The method according to claim 26, wherein the transcription activation domain-post-translational modifier polypeptide expression unit in the first cell and the transcription activation domain-mutant post-translational modifier polypeptide expression unit in the second cell are under control of a repressible promoter.

34. The method according to claim 26, wherein the first and second cells are selected from the group consisting of yeast cells, mammalian cells, and other cultured cells in which the post-translational modification of a target protein by a post-translational modifier polypeptide occurs.

35. The method according to claim 27, wherein the post-translational modifier polypeptide is a ubiquitin family protein.

36. The method according to claim 27, wherein the post-translational modifier polypeptide is a SUMO family protein selected from the group consisting of SUMO-1, SUMO-2, SUMO-3.

37. The method according to claim 27, wherein the post-translational modifier polypeptide is a NEDD8 protein.

38. The method according to claim 27, wherein the post-translational modifier polypeptide is a Apg12 protein.

39. The method according to claim 29, wherein the DNA binding domain is a DNA binding domain of a Gal4 transcriptional activator or a DNA binding domain of a LexA transcriptional repressor.

40. The method according to claim 30, wherein the transcription activation domain is selected from the group consisting of VP16, B42, and the activation domain of Gal4.

41. The method according to claim 32 further comprising:
treating the cells with an inducing agent to activate the inducible promoter.

42. The method according to claim 33 further comprising:
culturing the cells with an appropriate repressing agent, and removing the repressing agent when suitable to activate the repressible promoter.

43. The method according to claim 34, wherein the first and second cells are mammalian cells.

44. The method according to claim 34, wherein the first and second cells are yeast cells.

* * * * *